US009051349B2

(12) United States Patent
Callens et al.

(10) Patent No.: US 9,051,349 B2
(45) Date of Patent: Jun. 9, 2015

(54) LARAZOTIDE ACETATE COMPOSITIONS

(71) Applicant: Alba Therapeutics Corp., Baltimore, MD (US)

(72) Inventors: Roland Callens, Grimbergen (BE); Georges Blondeel, Aalst (BE); Thierry Delplanche, Mont-St-Guibert (BE)

(73) Assignee: Alba Therapeutics Corporation, Baltimore, MD (US)

( * ) Notice: Subject to any disclaimer, the term of this patent is extended or adjusted under 35 U.S.C. 154(b) by 0 days.

(21) Appl. No.: 13/832,820

(22) Filed: Mar. 15, 2013

(65) Prior Publication Data
US 2013/0281384 A1 Oct. 24, 2013

Related U.S. Application Data

(63) Continuation-in-part of application No. 12/743,411, filed as application No. PCT/EP2008/066037 on Nov. 21, 2008.

(60) Provisional application No. 61/014,938, filed on Dec. 19, 2007, provisional application No. 61/073,843, filed on Jun. 19, 2008, provisional application No. 61/103,289, filed on Oct. 7, 2008.

(30) Foreign Application Priority Data

Nov. 21, 2007 (EP) .................................... 07121207

(51) Int. Cl.
C07K 7/06 (2006.01)
C07C 53/10 (2006.01)
A61K 38/08 (2006.01)

(52) U.S. Cl.
CPC . C07K 7/06 (2013.01); C07C 53/10 (2013.01); A61K 38/08 (2013.01)

(58) Field of Classification Search
None
See application file for complete search history.

(56) References Cited

U.S. PATENT DOCUMENTS

| 3,960,830 | A | 6/1976 | Bayer et al. | |
|---|---|---|---|---|
| 4,725,645 | A | 2/1988 | Anteunis et al. | |
| 6,884,345 | B1 | 4/2005 | Irgum et al. | |
| 7,026,294 | B2 | 4/2006 | Fasano et al. | |
| 8,546,530 | B2 | 10/2013 | Callens et al. | |
| 2002/0115825 | A1* | 8/2002 | Fasano | 530/324 |
| 2005/0065074 | A1 | 3/2005 | Fasano et al. | |
| 2005/0165215 | A1 | 7/2005 | Bigelow et al. | |
| 2008/0103100 | A1* | 5/2008 | Fasano et al. | 514/16 |
| 2010/0280221 | A1 | 11/2010 | Callens et al. | |

FOREIGN PATENT DOCUMENTS

| EP | 0184243 | 6/1986 |
|---|---|---|
| JP | 61-268700 | 11/1986 |
| JP | 2003034653 | 2/2003 |
| WO | WO 96/37196 | 11/1996 |
| WO | WO 00/07609 | 2/2000 |
| WO | WO 01/89551 | 11/2001 |
| WO | WO 03/055900 | 7/2003 |
| WO | WO 2005/063800 | 7/2005 |
| WO | WO 2005/121164 | 12/2005 |
| WO | WO 2006/034056 | 3/2006 |
| WO | WO 2006/041945 | 4/2006 |
| WO | WO 2006/119388 | 11/2006 |
| WO | WO 2006/135811 | 12/2006 |
| WO | WO 2007/095092 | 8/2007 |
| WO | WO 2009/065836 | 5/2009 |
| WO | WO 2009/065949 | 5/2009 |

OTHER PUBLICATIONS

Kolpuru et al, "Analysis of binding affinity of the zonulin agonist (AT1002) and antagonist (AT1001) to the zonulin intestinal receptor," North American society for pediatric gastroenterology, hepatology, and nutritional annual meeting, J. Ped. Gastroent. Nutr., 43(4): E14-E76, p. E52, poster #121; Oct. 21, 2006).*

Di Pierro et al., "Zonula occludens toxin structure-function analysis: identification of the fragment biologically active on tight junctions and of the zonulin receptor binding domain," J. Biol. Chem. 276:19160-165 (2001)).*

Singhal et al. "Drug polymorphism and dosage form design: a practical perspective" Advanced Drug Delivery Reviews, 2004, 56, 335-347.*

Brittain et al. "Physical Characterization of Pharmaceutical Solids," Pharmaceutical Research, vol. 8, No. 8, 1991, pp. 963-973.*

Raw et al. "Regulatory considerations of pharmaceutical solid polymorphism in Abbreviated New Drug Applications (ANDAs)," Advanced Drug Delivery Reviews 56 (2004) 397-414.*

Shah et al. "Analytical Techniques for Quantification of Amorphous/Crystalline Phases in Pharmaceutical Solids," Journal of Pharmaceutical Sciences, vol. 95, No. 8, Aug. 2006, pp. 1641-1665.*

Newman et al. "Solid-state analysis of the active pharmaceutical ingredient in drug products," Drug Discovery Today vol. 8, No. 19 Oct. 2003, pp. 898-905.*

Bis et al. "Defining & Addressing Solid-State Risks After the Proof-of-Concept Stage of Pharmaceutical Development," Drug Development & Delivery, Apr. 2011, pp. 32-34.*

Andersson, L. et al., "Large-scale synthesis of peptides," Biopolymers, 55(3):227-250 (2000).

(Continued)

Primary Examiner — Christina Bradley
(74) Attorney, Agent, or Firm — Morgan, Lewis & Bockius LLP

(57) ABSTRACT

The invention provides crystalline forms of the peptide Gly-Gly-Val-Leu-Val-Gln-Pro-Gly (SEQ ID NO 1), and salts of the peptide, which may further have associated water molecules. These salts and hydrated salts of the peptide and compositions comprising these materials have advantageous pharmaceutical properties.

8 Claims, 11 Drawing Sheets

(56) References Cited

OTHER PUBLICATIONS

Di Pierro, M. et al., "Zonula occludens toxin structure-function analysis. Identification of the fragment biologically active on tight junctions and of the zonulin receptor binding domain," J. Biol. Chem., 276(22):19160-19165 (2001).

Wang, W. et al. "Human zonulin, a potential modulator of intestinal tight junctions," Journal of Cell Science, 113(Pt. 24):4435-4440 (2000).

Mostafavi, H. et al., "Synthesis of phospho-urodilatin by combination of global phosphorylation with the segment coupling approach," International Journal of Peptide & Protein Research, 48(2):200-207 (1996).

Najera, C., "From α-amino acids to peptides: All you need for the journey," Synlett, (9):1388-1404 (2002).

Montalbetii, C. A. G. N. et al., "Amide bond formation and peptide coupling," Tetrahedron, 61(46):10827-10852 (2005).

Guzman, F. et al., "Peptide synthesis: chemical or enzymatic," Electronic Journal of Biotechnology, 10(2):279-314 (2007).

Aimoto, S., "Contemporary methods for peptide and protein synthesis," Current Organic Chemistry, 5(1):45-87 (2001).

Hearn, M. T. et al., "High-performance liquid chromatography of amino acids, peptides and proteins. LXIX. Evaluation of retention and bandwidth relationships of myosin-related peptides separated by gradient elution reversed-phase high-performance liquid chromatography," Journal of Chromatography, 392:33-49 (1987).

Hearn, M. T. et al., "High-performance liquid chromatography of amino acids, peptides and proteins. LXXXV. Evaluation of the use of hydrophobicity coefficients for the prediction of peptide elution profiles," Journal of Chromatography, 438(2):197-210 (1988).

Pradayrol, L. et al., "Pig duodenal somatostatin: Extraction and purification," Metabolism, 27(9 Suppl. 1):1197-1200 (1978).

Lees, M. B. et al., "A study of elastase peptides from bovine white matter proteo lipid," Neurochemical Research, 6(10):1091-1104 (1981).

Duvick, J. P. et al., "Purification and characterization of a novel antimicrobial peptide from maize (Zea mays L.) kernels," Journal of Biological Chemistry, 267(26):18814-18820 (1992).

Wisniewski, R., "Principles of the design and operational considerations of large scale high performance liquid chromatography (HPLC) systems for proteins and peptides purification," Bioseparation, 3(2-3):77-143 (1992).

von Bahr-Lindstrom, H. et al., "Ion-exchange high-performance liquid-chromatography steps in peptide purifications," Bioscience Reports, 2(10):803-811 (1982).

Herraiz, T., "Sample preparation and reversed phase-high performance liquid chromatography analysis of food-derived peptides," Analytica Chemica Acta, 352(1):119-139 (1997).

Pedroso, E. et al., "Reversed-phase high-performance liquid chromatography of protected peptide segments," Journal of Chromatography, 409:281-290 (1987).

"Integrilin, Eptifibatide solution for injection," [online], XP002400963, Retrieved from the Internet: <URL: http://www.medsafe.govt.nz/profs/datasheet/i/integrilininj.htm>, [retrieved on Sep. 27, 2006], 12 pgs.

Ramagopal, U. A. et al., "Crystal structure of Boc-LAla-deltaPhe-deltaPhe-deltaPhe-deltaPhe-NHMe: a left-handed helical peptide," Journal of Peptide Research, 52(3):208-215 (1998).

Meienhofer, J. et al., "A solid-phase synthesis of (8-arginine)-vasopressin through a crystalline protected nonapeptide intermediate and biological properties of the hormone," Journal of the American Chemical Society, 92(24):7199-7202 (1970).

Lovejoy, B. et al., "Crystallization of proton channel peptides," Protein Science, 1(8):1073-1077 (1992).

Betz, S. F. et al., "Crystallization of a designed peptide from a molten globule ensemble," Folding & Design, 1(1):57-64 (1996).

Wissler, J. H., "Chemistry and biology of the anaphylatoxin related serum peptide system. I. Purification, crystallization and properties of classical anaphylatoxin from rat serum," European Journal of Immunology, 2(1):73-83 (1972).

Wissler, J. H., "Chemistry and biology of the anaphylatoxin related serum peptide system. II. Purification, crystallization and properties of cocytotaxin, a basic peptide from rat serum," European Journal of Immunology, 2(1):84-89 (1972).

Marinaro, M. et al., "Zonula occludens toxin acts as an adjuvant through different mucosal routes and induces protective immune responses," Infection and Immunity, 71(4):1897-1902 (2003).

International Search Report and Written Opinion for International Application No. PCT/EP2008/066037, mailed Jun. 16, 2009.

\* cited by examiner

FIGURE 10

Table 3 – Larazotide Acetate Stability – 40C/75%RH

| | | lot 020 | | | Lyophilized : E120040 4g/l | | | Lyophilized : E120040 1g/l | | |
|---|---|---|---|---|---|---|---|---|---|---|
| RRT | Name | time 0 % R.S | 1 month % R.S. | 2 months % R.S. | time 0 % R.S. | 1 month % R.S. | 2 months % R.S. | time 0 % R.S. | 1 month % R.S. | 2 months % R.S. |
| 0.90 | GlyGlyValLeuValNH2 | ND | 0.02 | 0.01 | 0.03 | 0.11 | 0.20 | 0.03 | 0.13 | 0.27 |
| 1.00 | Larazotide Acetate | 99.7 | 99.3 | 99.3 | 99.0 | 90.5 | 83.9 | 99.1 | 91.2 | 84.9 |
| 1.07 | Desamidated Larazotide | 0.21 | 0.27 | 0.27 | 0.25 | 0.90 | 1.73 | 0.25 | 0.86 | 1.63 |
| 1.10 | Larazotide methylester | 0.02 | 0.02 | 0.01 | 0.03 | 0.03 | 0.04 | 0.03 | 0.03 | 0.04 |
| 1.19 | Larazotide (5-8) | 0.02 | 0.04 | 0.04 | 0.20 | 0.37 | 0.54 | 0.15 | 0.37 | 0.63 |
| 1.23 | Acetylated Larazotide | 0.01 | 0.04 | 0.04 | 0.11 | 2.53 | 4.26 | 0.08 | 2.15 | 3.73 |
| 1.47 | Dimer | ND | 0.03 | 0.05 | 0.12 | 2.71 | 4.27 | 0.11 | 2.37 | 3.89 |

SEQUENCE LISTING

<160> NUMBER OF SEQ ID NOS: 24

<210> SEQ ID NO 1
<211> LENGTH: 8
<212> TYPE: PRT
<213> ORGANISM: Artificial Sequence -continued

```
<220> FEATURE:
<223> OTHER INFORMATION: peptide antagonist of zonulin

<400> SEQUENCE: 1

Gly Gly Val Leu Val Gln Pro Gly
1               5

<210> SEQ ID NO 2
<211> LENGTH: 4
<212> TYPE: PRT
<213> ORGANISM: Artificial Sequence
<220> FEATURE:
<223> OTHER INFORMATION: partial peptide antagonist of zonulin
<220> FEATURE:
<221> NAME/KEY: MISC_FEATURE
<222> LOCATION: (4)..(4)
<223> OTHER INFORMATION: May be modified with a carboxylic acid
      protecting group

<400> SEQUENCE: 2

Val Gln Pro Gly
1

<210> SEQ ID NO 3
<211> LENGTH: 4
<212> TYPE: PRT
<213> ORGANISM: Artificial Sequence
<220> FEATURE:
<223> OTHER INFORMATION: partial peptide antagonist of zonulin
<220> FEATURE:
<221> NAME/KEY: MISC_FEATURE
<222> LOCATION: (1)..(1)
<223> OTHER INFORMATION: May be modified with an amino protecting group

<400> SEQUENCE: 3

Gly Gly Val Leu
1

<210> SEQ ID NO 4
<211> LENGTH: 4
<212> TYPE: PRT
<213> ORGANISM: Artificial Sequence
<220> FEATURE:
<223> OTHER INFORMATION: partial peptide antagonist of zonulin

<400> SEQUENCE: 4

Val Gln Pro Gly
1

<210> SEQ ID NO 5
<211> LENGTH: 8
<212> TYPE: PRT
<213> ORGANISM: Artificial Sequence
<220> FEATURE:
<223> OTHER INFORMATION: peptide antagonist of zonulin
<220> FEATURE:
<221> NAME/KEY: MISC_FEATURE
<222> LOCATION: (1)..(1)
<223> OTHER INFORMATION: May be modified with an amino protecting group
<220> FEATURE:
<221> NAME/KEY: MISC_FEATURE
<222> LOCATION: (8)..(8)
<223> OTHER INFORMATION: May be modified with a carboxylic acid
      protecting group

<400> SEQUENCE: 5

Gly Gly Val Leu Val Gln Pro Gly
1               5
```

```
-continued

<210> SEQ ID NO 6
<211> LENGTH: 8
<212> TYPE: PRT
<213> ORGANISM: Artificial Sequence
<220> FEATURE:
<223> OTHER INFORMATION: peptide antagonist of zonulin
<220> FEATURE:
<221> NAME/KEY: MISC_FEATURE
<222> LOCATION: (1)..(1)
<223> OTHER INFORMATION: May be modified with a tert-butyloxycarbonyl
      amino protecting group
<220> FEATURE:
<221> NAME/KEY: MISC_FEATURE
<222> LOCATION: (8)..(8)
<223> OTHER INFORMATION: May be modified with a tert-butyl ester carboxy
      protecting group

<400> SEQUENCE: 6

Gly Gly Val Leu Val Gln Pro Gly
1               5

<210> SEQ ID NO 7
<211> LENGTH: 4
<212> TYPE: PRT
<213> ORGANISM: Artificial Sequence
<220> FEATURE:
<223> OTHER INFORMATION: partial peptide antagonist of zonulin
<220> FEATURE:
<221> NAME/KEY: MISC_FEATURE
<222> LOCATION: (1)..(1)
<223> OTHER INFORMATION: May be modified with an amino protecting group

<400> SEQUENCE: 7

Val Gln Pro Gly
1

<210> SEQ ID NO 8
<211> LENGTH: 4
<212> TYPE: PRT
<213> ORGANISM: Artificial Sequence
<220> FEATURE:
<223> OTHER INFORMATION: partial peptide antagonist of zonulin
<220> FEATURE:
<221> NAME/KEY: MISC_FEATURE
<222> LOCATION: (1)..(1)
<223> OTHER INFORMATION: May be modified with an amino protecting group
<220> FEATURE:
<221> NAME/KEY: MISC_FEATURE
<222> LOCATION: (4)..(4)
<223> OTHER INFORMATION: May be modified with a carboxylic acid
      protecting group

<400> SEQUENCE: 8

Val Gln Pro Gly
1

<210> SEQ ID NO 9
<211> LENGTH: 4
<212> TYPE: PRT
<213> ORGANISM: Artificial Sequence
<220> FEATURE:
<223> OTHER INFORMATION: partial peptide antagonist of zonulin

<400> SEQUENCE: 9

Gly Gly Val Leu
1

<210> SEQ ID NO 10
<211> LENGTH: 5
<212> TYPE: PRT
<213> ORGANISM: Artificial Sequence
```

```
<220> FEATURE:
<223> OTHER INFORMATION: partial peptide antagonist of zonulin

<400> SEQUENCE: 10

Leu Val Gln Pro Gly
1               5

<210> SEQ ID NO 11
<211> LENGTH: 6
<212> TYPE: PRT
<213> ORGANISM: Artificial Sequence
<220> FEATURE:
<223> OTHER INFORMATION: partial peptide antagonist of zonulin

<400> SEQUENCE: 11

Val Leu Val Gln Pro Gly
1               5

<210> SEQ ID NO 12
<211> LENGTH: 7
<212> TYPE: PRT
<213> ORGANISM: Artificial Sequence
<220> FEATURE:
<223> OTHER INFORMATION: partial peptide antagonist of zonulin

<400> SEQUENCE: 12

Gly Val Leu Val Gln Pro Gly
1               5

<210> SEQ ID NO 13
<211> LENGTH: 12
<212> TYPE: PRT
<213> ORGANISM: Artificial Sequence
<220> FEATURE:
<223> OTHER INFORMATION: peptide antagonist of zonulin

<400> SEQUENCE: 13

Gly Gly Val Leu Val Gln Pro Gly Val Gln Pro Gly
1               5                   10

<210> SEQ ID NO 14
<211> LENGTH: 16
<212> TYPE: PRT
<213> ORGANISM: Artificial Sequence
<220> FEATURE:
<223> OTHER INFORMATION: partial peptide antagonist of zonulin

<400> SEQUENCE: 14

Gly Gly Val Leu Val Gln Pro Gly Gly Gly Val Leu Val Gln Pro Gly
1               5                   10                  15

<210> SEQ ID NO 15
<211> LENGTH: 8
<212> TYPE: PRT
<213> ORGANISM: Artificial Sequence
<220> FEATURE:
<223> OTHER INFORMATION: partial peptide antagonist of zonulin
<220> FEATURE:
<221> NAME/KEY: MISC_FEATURE
<222> LOCATION: (1)..(1)
<223> OTHER INFORMATION: May be modified with an acetamide amino
      protecting group

<400> SEQUENCE: 15

Gly Gly Val Leu Val Gln Pro Gly
1               5
```

-continued

```
<210> SEQ ID NO 16
<211> LENGTH: 4
<212> TYPE: PRT
<213> ORGANISM: Artificial Sequence
<220> FEATURE:
<223> OTHER INFORMATION: partial peptide antagonist of zonulin
<220> FEATURE:
<221> NAME/KEY: MISC_FEATURE
<222> LOCATION: (1)..(1)
<223> OTHER INFORMATION: May be modified with a benzyloxycarbonyl amino
      protecting group

<400> SEQUENCE: 16

Val Gln Pro Gly
1

<210> SEQ ID NO 17
<211> LENGTH: 4
<212> TYPE: PRT
<213> ORGANISM: Artificial Sequence
<220> FEATURE:
<223> OTHER INFORMATION: partial peptide antagonist of zonulin
<220> FEATURE:
<221> NAME/KEY: MISC_FEATURE
<222> LOCATION: (1)..(1)
<223> OTHER INFORMATION: May be modified with a tert-butyloxycarbonyl
      amino protecting group

<400> SEQUENCE: 17

Gly Gly Val Leu
1

<210> SEQ ID NO 18
<211> LENGTH: 4
<212> TYPE: PRT
<213> ORGANISM: Artificial Sequence
<220> FEATURE:
<223> OTHER INFORMATION: partial peptide antagonist of zonulin
<220> FEATURE:
<221> NAME/KEY: MISC_FEATURE
<222> LOCATION: (4)..(4)
<223> OTHER INFORMATION: May be modified with a tert-butyl ester carboxy
      protecting group

<400> SEQUENCE: 18

Val Gln Pro Gly
1

<210> SEQ ID NO 19
<211> LENGTH: 8
<212> TYPE: PRT
<213> ORGANISM: Artificial Sequence
<220> FEATURE:
<223> OTHER INFORMATION: peptide antagonist of zonulin
<220> FEATURE:
<221> NAME/KEY: MISC_FEATURE
<222> LOCATION: (1)..(1)
<223> OTHER INFORMATION: May be modified with a tert-butyloxycarbonyl
      amino protecting group
<220> FEATURE:
<221> NAME/KEY: MISC_FEATURE
<222> LOCATION: (8)..(8)
<223> OTHER INFORMATION: May be modified with a tert-butyl ester carboxy
      protecting group

<400> SEQUENCE: 19

Gly Gly Val Leu Val Gln Pro Gly
1               5
```

```
<210> SEQ ID NO 20
<211> LENGTH: 8
<212> TYPE: PRT
<213> ORGANISM: Artificial Sequence
<220> FEATURE:
<223> OTHER INFORMATION: peptide antagonist of zonulin
<220> FEATURE:
<221> NAME/KEY: MISC_FEATURE
<222> LOCATION: (1)..(1)
<223> OTHER INFORMATION: May be modified with a tert-butyloxycarbonyl
      amino protecting group

<400> SEQUENCE: 20

Gly Gly Val Leu Val Gln Pro Gly
1               5

<210> SEQ ID NO 21
<211> LENGTH: 4
<212> TYPE: PRT
<213> ORGANISM: Artificial Sequence
<220> FEATURE:
<223> OTHER INFORMATION: partial peptide antagonist of zonulin
<220> FEATURE:
<221> NAME/KEY: MISC_FEATURE
<222> LOCATION: (1)..(1)
<223> OTHER INFORMATION: May be modified with a benzyloxycarbonyl amino
      protecting group
<220> FEATURE:
<221> NAME/KEY: MISC_FEATURE
<222> LOCATION: (4)..(4)
<223> OTHER INFORMATION: May be modified with a tert-butyl ester carboxy
      protecting group

<400> SEQUENCE: 21

Val Gln Pro Gly
1

<210> SEQ ID NO 22
<211> LENGTH: 4
<212> TYPE: PRT
<213> ORGANISM: Artificial Sequence
<220> FEATURE:
<223> OTHER INFORMATION: partial peptide antagonist of zonulin
<220> FEATURE:
<221> NAME/KEY: MISC_FEATURE
<222> LOCATION: (1)..(1)
<223> OTHER INFORMATION: May be modified with a benzyloxycarbonyl amino
      protecting group
<220> FEATURE:
<221> NAME/KEY: MISC_FEATURE
<222> LOCATION: (4)..(4)
<223> OTHER INFORMATION: May be modified with a tert-butyl ester carboxy
      protecting group

<400> SEQUENCE: 22

Val Gln Pro Gly
1

<210> SEQ ID NO 23
<211> LENGTH: 8
<212> TYPE: PRT
<213> ORGANISM: Artificial Sequence
<220> FEATURE:
<223> OTHER INFORMATION: peptide antagonist of zonulin
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
```

```
<400> SEQUENCE: 23

Gly Xaa Xaa Xaa Val Gly Xaa Gly
1               5

<210> SEQ ID NO 24
<211> LENGTH: 5
<212> TYPE: PRT
<213> ORGANISM: Artificial Sequence
<220> FEATURE:
<223> OTHER INFORMATION: partial peptide antagonist of zonulin

<400> SEQUENCE: 24

Gly Gly Val Leu Val
1               5
```

LARAZOTIDE ACETATE COMPOSITIONS

PRIORITY

This Application is a continuation-in-part of U.S. application Ser. No. 12/743,411 filed May 18, 2010, which is a national stage Application of PCT/EP2008/066037 filed Nov. 21, 2008, which claims priority to U.S. Provisional Application No. 61/103,289 filed Oct. 7, 2008, U.S. Provisional Application No. 61/073,843 filed Jun. 19, 2008, U.S. Provisional Application No. 61/014,938 filed Dec. 19, 2007, and EP 07121207.0 filed Nov. 21, 2007, all of which are hereby incorporated by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ALBA_062_00US_SeqList_ST25.txt, date recorded: May 22, 2013, file size 8 kilobytes).

TECHNICAL FIELD

The present invention relates to a process for the manufacture of a certain octapeptide ("Larazotide"), and in particular to such a process comprising a purification step. The invention further relates to salts of the peptide, and in particular to solid state forms of such salts including crystalline (or highly organized) forms that may also incorporate water (stoichiometric and non-stoichiometric hydrates of such salts).

BACKGROUND

*Zonula occludens* toxin ("zot") is an enterotoxin produced by *Vibrio cholerae*. Zot increases permeability by reversibly affecting the structure of tight junctions as described in WO 1996/37196. The comparison of its sequence with a potential human analogue ("zonulin") revealed an 8-amino acid shared motif (GXXXVGXG, SEQ ID NO 23), described by DI PIERRO, et al. *Zonula Occludens Toxin Structure—Function Analysis. J. Biol. Chem.* 276(22): 19160-19165 (2001).

The octapeptide of the following sequence: Gly-Gly-Val-Leu-Val-Gln-Pro-Gly (SEQ ID NO 1) has been described as a peptide antagonist of zonulin by Fasano in WO 0007609 and by WANG, et al. *Human Zonulin, a Potential Modulator of Intestinal Tight Junctions. Journal of Cell Science.* 2000, 113:4435-4440 (2000). Fasano discloses its application in methods for treatment of gastrointestinal inflammation as well as of conditions associated with breakdown of the blood brain barrier. Fasano et al. also describe in U.S. Pat. No. 7,026,294 its use in a method for delay of onset of diabetes. Fasano describes delivery of the peptide to, inter alia, the small intestine via peptide-coated beads having a gastroresistant coating.

This octapeptide ("Larazotide") is a promising treatment of various diseases that involve disordered intercellular communication, which include developmental and intestinal disorders leading to autoimmune disease (coeliac disease and type 1 diabetes), tissue inflammation, malignant transformation, and metastasis. None of the above references describe any process for the synthesis of this octapeptide. The present invention now makes available a process for its manufacture. The present invention also makes available various salts of the peptide suitable for pharmaceutical use. The present invention further provides solid state forms of such salts of the peptide and pharmaceutical compositions comprising the same. In one embodiment of the present invention, the salt of the peptide is crystalline (or highly organized). In a second embodiment, the crystalline form of the salt of the peptide may further comprise (stoichiometric and non-stoichiometric) waters of hydration (a "hydrate"). The present invention additionally provides pharmaceutical compositions comprising a crystalline stoichiometric or non-stoichiometric hydrate of a salt of the peptide. It is well recognized that pharmaceutical solids can exist in more than one solid state form (i.e., crystalline, noncrystalline/amorphous, quasicrystalline/organized aggregate). Polymorphism is defined as the ability of a solid compound to exist in more than one crystalline form with the same covalent chemical structure, but different supra-molecular structures and ordered arrangements of molecules within the crystalline lattice. In addition to exhibiting polymorphism, many pharmaceutical solids form hydrates and organic solvates, which themselves can be crystalline and exhibit polymorphism. Hydrates can be stoichiometric or non-stoichiometric. In a stoichiometric hydrate the water molecules are tightly associated with or bound to the pharmaceutical compound as well as to other water molecules and as a result are integral to the crystal lattice. In contrast, the water molecules of a non-stoichiometric hydrate (sometimes referred to as a variable hydrate) are loosely associated with the pharmaceutical compound and the crystal lattice. For example, in certain systems the water molecules of a variable hydrate reside in channels in the crystal lattice (Vogt et al. *J Pharm Biomed Anal* 40 (2006) 1080-1088). Generally speaking, the amount of water present in a non-stoichiometric or variable hydrate can be typically a function of the relative humidity (RH) environment of the sample. Hydrates, in particular non-stoichiometric hydrates, can be a difficult prospect for development because of the additional effort needed to investigate and characterize the different hydration states of the pharmaceutical compound. At the same time, the manufacturing process has to be scrutinized to determine what conditions are needed to ensure that the API contains a predictable composition.

It is well recognized that different solid state forms of the same compound can exhibit significantly different chemical and physical properties including color, morphology, stability, solubility, dissolution and bioavailability. As with all pharmaceutical compounds and compositions, the chemical and physical properties of a particular solid state form of a compound are important to its commercial development. These properties include, but are not limited to: (1) packing properties such as molar volume, density and hygroscopicity; (2) thermodynamic properties such as melting temperature, vapor pressure and solubility; (3) kinetic properties such as dissolution rate and stability (including stability at ambient conditions, especially to moisture, and under storage conditions); (4) surface properties such as surface area, wettability, interfacial tension and shape; (5) mechanical properties such as hardness, tensile strength, compactability, handling, flow and blend; and (6) filtration properties. These properties can affect, for example, processing and storage of pharmaceutical compositions, sometimes referred to as drug product and/or of the active pharmaceutical ingredient (API), sometimes referred to as drug substance. As mentioned above, different solid state forms of the API can have different rates of solubility which can translate into differences in bioavailability in vivo.

In general, the solid state form of a compound can be distinguished from another solid state form of the same compound by one or more of the following techniques: x-ray powder diffraction (XRPD), thermal techniques including thermogravimetric analysis (TGA) and differential scanning calorimetry (DSC), as well as Infrared (IR), Raman and/or solid state NMR (ssNMR) spectroscopy.

The Applicant describes here a process for the synthesis of the octapeptide Gly-Gly-Val-Leu-Val-Gln-Pro-Gly (SEQ ID NO 1), which allows for an efficient production of said octapeptide with a good yield and a high quality and purity level while presenting advantages in terms of productivity and required manufacturing equipment.

DESCRIPTION OF THE FIGURES

FIG. 10 shows the results of a Larazotide Acetate stability study at 40° C. and 75% RH (SEQ ID NO 24).

DETAILED DESCRIPTION OF INVENTION

Figure 1:
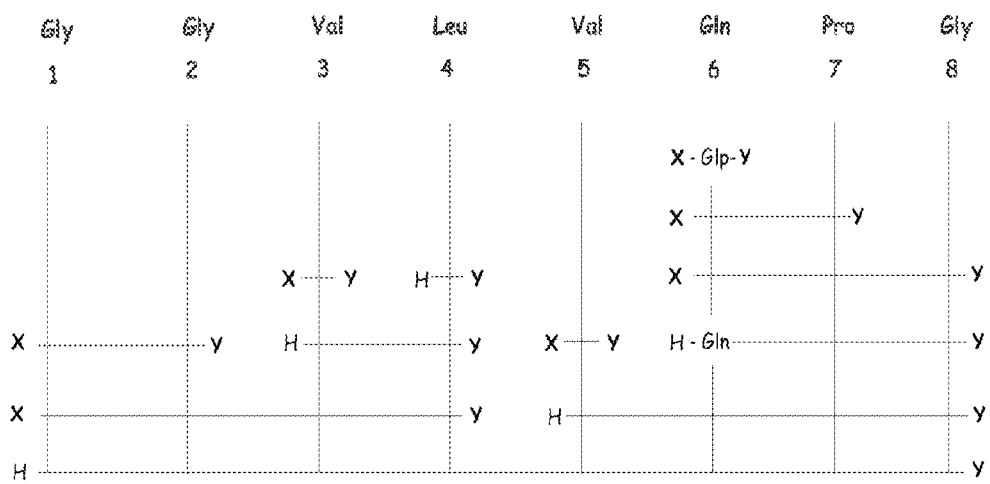
FIG. 1 illustrates a scheme 1 for synthesizing the octapeptide of SEQ ID NO 1.

The present invention concerns a process for the synthesis of a Gly-Gly-Val-Leu-Val-Gln-Pro-Gly octapeptide (SEQ ID NO 1) comprising at least one peptide coupling step carried out in solution.

The process according to the present invention allows the use of a convergent synthetic strategy, with a limited number of steps, and avoids successive protection/deprotection reactions.

The process according to the invention provides the octapeptide in an industrial scale without substantial formation of by-products or racemisation. Moreover, the by-products possibly formed during the process according to the present invention are readily separable from the final octapeptide by a specific purification process. The present invention allows the synthesis of peptides containing both L- and D-amino acid configurations. Moreover it has been found that intermediates and products of the process according to the invention can be isolated and purified easily by solid/liquid separation techniques such as precipitation or crystallization. The process according to the invention even allows, if desired, to substantially avoid any time consuming purification steps such as chromatography. This is unusual and unexpected in the framework of the synthesis of an octapeptide.

In a first particular aspect, the process according to the present invention comprises coupling a peptide of formula: Val-Gln-Pro-Gly-Y (SEQ ID NO 2); wherein the C-terminal amino acid is protected by a carboxylic acid protecting group Y; with a Leucine or a C-terminal Leucine peptide, preferably selected from formulae: X-Gly-Gly-Val-Leu (SEQ ID NO 3), X-Gly-Val-Leu and X-Val-Leu; and wherein said Leucine or C-terminal Leucine peptide is optionally activated by a carboxylic acid activating agent.

The carboxylic acid protecting group Y is preferably selected from alkyl esters, aryl esters, aralkyl esters and silyl groups. Y is more preferably selected from alkyl esters and silyl groups. Excellent results were obtained with alkyl esters and in particular with the tert-butyl ester of the Val-Gln-Pro-Gly (SEQ ID NO 4) peptide.

On the other hand, the amino protecting group X is preferably selected from allyloxycarbonyl groups, tert-butyloxycarbonyl (BOC), benzyloxycarbonyl (Z), 9-fluorenylmethyloxycarbonyl (Fmoc), 4-nitrobenzenesulfonyl (Nosyl), 2-nitrobenzenesulfenyl (Nps) and optionally substituted derivatives thereof. Excellent results were obtained with the tert-butyloxycarbonyl (BOC) group.

For the purpose of the present invention, the term "peptide" refers to a polymer in which the monomers are amino acids covalently attached together through amide bonds.

Peptides are two or often more amino acids monomers long. In addition, all peptide sequences are represented by formulae whose left to right orientation is in the conventional direction of amino-terminus to carboxy-terminus.

For the purpose of the present invention, the term "amino acid" is intended to denote any compound comprising at least one NR1R2 group, preferably $NH_2$ group, and at least one carboxyl group. The amino acids of this invention can be naturally occurring or synthetic. The natural amino acids, with exception of glycine, contain a chiral carbon atom. Unless otherwise specifically indicated, the compounds containing natural amino acids with the L-configuration are preferred. Amino acids residues are abbreviated as follows throughout the application: Glycine is Gly or G; Valine is Val or V; Leucine is Leu or L; Glutamine is Gln or Q; Proline is Pro or P; Pyroglutamic acid (or pyrrolidone carboxylic acid) is Glp.

For the purpose of the present invention, the term "C-terminal" of a peptide is the end of the amino acid chain terminated by a free carboxyl group (—COOH). On the other hand, the term "N-terminal" refers to the end of a peptide terminated by an amino acid with a free amine group (—$NH_2$).

For the purpose of the present invention, the term "coupling" refers to the reaction between the carboxyl group of an amino acid or the C-terminus of a first peptide to the amino group of another amino acid or the N-terminus of a second peptide. In other words, during coupling, two peptide intermediate fragments, or a peptide intermediate fragment and a reactive amino acid, are coupled, generally, in an appropriate solvent, and usually in the presence of additional reagents that promote the efficiency and quality of the coupling reaction. The peptide intermediate fragments are reactively arranged so the N-terminus of one fragment becomes coupled to the C-terminus of the other fragment, or vice versa.

For the purposes of the present invention, the term "crystalline" refers to a solid state form of a compound in which the constituent atoms are organized into a repeating motif and produces a characteristic x-ray powder diffraction (XRPD) pattern. See generally, USP 35, NF 30, <941> (May 1, 2012) pp 427 et seq.

In a further particular aspect, the process according to the present invention comprises coupling a peptide of formula Val-Gln-Pro-Gly-Y (SEQ ID NO 2) with a peptide of formula X-Gly-Gly-Val-Leu (SEQ ID NO 3).

In the present invention, the protecting group is any sort of group that can prevent the atom or moiety to which it is attached, e.g., oxygen or nitrogen, from participating in undesired reactions during processing and synthesis. Protecting groups include side chain protecting groups and C- or N-terminal protecting groups. Protecting groups can also prevent reaction or bonding of carboxylic acids, thiols and the like.

The term "amino protecting group X" refers to protecting groups which can be used in the present invention to replace an acidic proton of an amino group in order to reduce its nucleophilicity. As it will be illustrated herein below, the amino protecting group X can be removed, if appropriate, in a deprotection reaction prior to possible subsequent addition of a next amino acid.

The amino protecting group X is preferably sterically hindering. The term "sterically hindering" is intended to denote in particular a substituent comprising at least 3 carbon atoms, in particular at least 4 carbon atoms, including at least one secondary, tertiary or quaternary carbon atom. The sterically hindering group often comprises at most 100, preferably at most 50 carbon atoms.

By way of non-limiting examples of suitable amino protecting groups represented herein by X, which can be used in the process according to the present invention, mention may in particular be made of substituted or unsubstituted groups of acyl type, such as the formyl, acrylyl (Acr), benzoyl (Bz), acetyl (Ac), trifluoroacetyl, substituted or unsubstituted groups of aralkyloxycarbonyl type, such as the benzyloxycarbonyl (Z), p-chlorobenzyloxycarbonyl, p-bromobenzyloxycarbonyl, p-nitrobenzyloxycarbonyl, p-methoxybenzyloxycarbonyl, benzhydryloxycarbonyl, 2-(p-biphenylyl) isopropyloxycarbonyl, 2-(3,5-dimethoxyphenyl) isopropyloxycarbonyl, p-phenylazobenzyloxycarbonyl, triphenylphosphonoethyloxycarbonyl or 9-fluorenylmethyloxycarbonyl group (Fmoc), substituted or unsubstituted groups of alkyloxycarbonyl type, such as the tert-butyloxycarbonyl (BOC), tert-amyloxycarbonyl, diisopropylmethyloxycarbonyl, isopropyloxycarbonyl, ethyloxycarbonyl, allyloxycarbonyl, 2-methylsulphonylethyloxycarbonyl or 2,2,2-trichloroethyloxycarbonyl group, groups of cycloalkyloxycarbonyl type, such as the cyclopentyloxycarbonyl, cyclohexyloxycarbonyl, adamantyloxycarbonyl or isobornyloxycarbonyl group, and groups containing a hetero atom, such as the benzenesulphonyl, p-toluenesulphonyl, mesitylenesulphonyl, methoxytrimethylphenyl-sulphonyl, 2-nitrobenzenesulfonyl, 2-nitrobenzenesulfenyl, 4-nitrobenzenesulfonyl or 4-nitrobenzenesulfenyl group. Among these groups X, those comprising a carbonyl, a sulfenyl or a sulphonyl group are preferred. An amino protecting group X is preferably selected from allyloxycarbonyl groups, tert-butyloxycarbonyl (BOC), benzyloxycarbonyl (Z), 9-fluorenylmethyloxycarbonyl (Fmoc), 4-nitrobenzenesulfonyl (Nosyl), 2-nitrobenzenesulfenyl (Nps) and substituted derivatives. More preferably, the amino protecting group X is tert-butyloxycarbonyl (BOC).

Amino protecting groups X may be introduced by various methods e.g. by reaction with suitable acid halides such as carbobenzoxyl chloride or acid anhydrides such as acetic anhydride. On the other hand, amino protecting groups X may be removed, for example, by acidolysis, hydrogenolysis, treatment with dilute ammonium hydroxide, treatment with sodium, treatment with sodium amide, treatment with hydrazine, or enzymatic hydrolysis.

The term "carboxylic acid protecting group Y" refers to protecting groups which can be used in the present invention to replace the acidic proton of a carboxylic acid. Preferred groups are selected from optionally substituted alkyl, aryl, aralkyl and, preferably, silyl groups. Trialkylsilyl groups are still more particularly preferred. Examples of such groups include methoxymethyl, methylthiomethyl, 2,2,2-trichloroethyl, 2-haloethyl, 2-(trimethylsilyl)ethyl, t-butyl, aryl, alkyl, aralkyl, allyl, benzyl, triphenylmethyl (trityl), benzhydryl, p-nitrobenzyl, p-methoxybenzyl, and trialkylsilyl groups such as trimethylsilyl, triethylsilyl, t-butyldimethylsilyl, i-propyl-dimethylsilyl. A trimethylsilyl group is more particularly preferred. In the process according to the present invention, the Val-Gln-Pro-Gly (SEQ ID NO 4) peptide is more preferably protected by a group selected from a persilylated derivative and an alkyl ester. Good results were obtained by using MSA (N-Methyl-N-trimethylsilylacetamide). The persilylation of an amino acid or of a peptide can be carried out, for example, according to the method described in Patent Application EP 184243 B (SOLVAY). Excellent results were also obtained by using the Val-Gln-Pro-Gly-Y (SEQ ID NO 2) peptide where Y is a tert-butyl ester group.

The carboxylic acid protecting groups Y may be introduced by various methods including esterification and silylation. On the other hand, the removal of carboxylic acid protecting groups Y may, for example, be effected by hydrolysis, saponification, acidolysis, hydrogenolysis or enzymatic hydrolysis.

It will be appreciated that the intermediate peptides, i.e. shorter peptides than the octapeptide having appropriate sequence of amino acids, to be coupled by the process according to the present invention may, if desired, be prepared using the solid-phase method of peptide synthesis. In such a method the carboxylic acid protecting group of the C-terminal amino acid is usually bound to a resin.

In another particular aspect of the present invention, the process as above described may thus be carried out in the presence of a carboxylic acid activating agent.

For the purposes of the present invention, the term "carboxylic acid activating agent", also referred to as "coupling agent", is a reagent that replaces the hydroxyl group of a carboxylic acid with a suitable leaving group which is susceptible to nucleophilic displacement, allowing the coupling of an amino acid or peptide free carboxy group with a free amino group of another amino acid or peptide to form an amide bond between the reactants.

Examples of carboxylic acid activating agent and activated groups which are useful in the present invention include carbodiimides, carbonyldiimidazoles, carbonyl halides, in particular acyl halides or haloformiates, azides, phosphonium salts and uronium or guanidinium salts, symmetric or mixed anhydrides or active ester. Such carboxylic acid activating agent may be used before the coupling step in order to isolate the activated peptide derivative or used in situ prior to the introduction of the free amino peptide derivative.

Non-limitative particular examples of such carboxylic acid activating agent include carbodiimide reagents such as N,N'-dicyclohexylcarbodiimide (DCC), N-Ethyl-N'-(3-dimethylaminopropyl)carbodiimide (EDC), 1-(3-dimethylaminopropyl)-3-ethylcarbodiimide hydrochloride (EDCI also referred to as "WSC"), carbodiimidazoles reagents such as 1,1'-carbonyldiimidazole (CDI), diisopropylcarbodiimide (DIPCDI), diisopropylcarbodiimide (DIC) or derivatives thereof; phosphonium salts such as (benzotriazol-1-yloxy) tris-(dimethylamino)phosphonium (BOP), benzotriazol-1-yl-oxytripyrrolidinophosphonium hexafluorophosphate (Py-BOP), (7-Azabenzotriazol-1-yloxy)

tripyrrolidinophosphonium hexafluorophosphate (PyAOP), bromo-tris-pyrrolidino phosphoniumhexafluorophosphate (PyBroP), chloro-tris-pyrrolidino phosphoniumhexafluorophosphate (PyCloP) or derivatives thereof; uronium or guanidinium salts such as o-benzotriazole-N,N,N',N'-tetramethyluronium-hexafluorophosphate (HBTU), o-(benzotriazol-1-yl)-N,N,N',N'-tetramethyluronium tetrafluoroborate (TBTU), 2-(7-aza-1-H-benzotriazole-1-yl)-1,1,3,3-tetramethyluronium hexafluorophosphate (HATU), O-(7-azabenzotriazol-1-yl)-1,1,3,3 bis(tetramethylene)uronium hexafluorophosphate (HAPyU) or derivatives thereof; acyl halides such as isobutyl chloroformate (iBCF), pivaloyl chloride (PivCl), t-butylchloroformate (TBCF), ethyl chloroformate (ECF) or derivatives thereof; esterificating agent such as pentafluorophenol (PfP), N-hydroxysuccinimide (NHS) or derivatives thereof; azidination agent such as diphenylphosphoryl azide (DPPA) or derivatives thereof. Preactivated amino acids or under the form of N-carboxyanhydrides, and in particular urethane-N-carboxyanhydrides (UNCA's) are also good examples of carboxylic acid activating agents.

The carboxylic acid activating agent is preferably chosen from carbodiimides, carbonyldiimidazoles, acyl halides, phosphonium salts and uronium or guanidinium salts and more preferably from isobutyl chloroformate and pivaloyl-chloride. Carbonyl halide, more particularly acyl halide, in particular acyl chloride coupling agents as described above are preferred. Tertiary acyl halides are more particularly preferred. Examples of tertiary acyl halides are inter alia 1-adamantoyl chloride, 2,2-dimethylbutyroyl chloride and pivaloyl chloride. Pivaloyl chloride is more particularly preferred as carboxylic acid activating agent.

It has been found, surprisingly, that it is possible, in particular, by carefully selecting the carboxylic acid activating agent to substantially or completely avoid racemisation, in particular of any Leu group when coupling Leu or Leu-C-terminal fragments as described herein before. Moreover coupling conditions have been identified which are described here after, which allow for high overall high productivity and yield in particular of desired octapeptide while maintaining excellent optical purity.

Good results are often obtained when using additional reagents which reduce side reactions and/or increase reaction efficiency. For example, phosphonium and uronium salts can, in the presence of a tertiary base, for example, diisopropylethylamine (DIPEA) and triethylamine (TEA), convert protected amino acids into activated species (for example, BOP, PyBOP, HBTU, and TBTU all generate HOBt esters). Other reagents which help prevent racemization include carbodiimides (for example, DCC or WSCDI) with an added auxiliary nucleophile (for example, 1-hydroxy-benzotriazole (HOBt), 3,4-dihydro-3-hydroxy-4-oxo-1,2,3-benzotriazine (HOOBT), 1-hydroxy-azabenzotriazole (HOAt), or HOSu) or derivatives thereof. TBTU may also be used. The mixed anhydride method, using isobutyl chloroformate, with or without an added auxiliary nucleophile, is also used, as is the azide method, due to the low racemization obtained. These types of compounds can also increase the rate of carbodiimide-mediated couplings, as well as prevent dehydration of Asn and Gln residues.

When such carboxylic acid activating agents are used, the coupling reaction is often carried out in the presence of a base as additional reagent. In another particular aspect of the present invention, the coupling reaction is thus carried out in the presence of a base. The base is preferably chosen from tertiary and heteroaromatic amines such as N-methylmorpholine (NMM), pyridine, triethylamine (TEA), diisopropylethylamine (DIPEA) or mixtures thereof. More preferably, it is chosen from N-methylmorpholine and diisopropylethylamine.

In another particular aspect of the present invention, the peptide coupling as above described is carried out in a polar organic solvent. In a particular preferred embodiment, the polar organic solvent allows for particularly efficient control of racemization of the peptide bond formed, the solubility of the peptide and/or peptide fragments, and the coupling reaction rate. The polar organic solvent is preferably selected from amide type solvents such as N,N-dimethylacetamide (DMA), N,N-dimethylformamide (DMF), N-methylpyrrolidone (NMP), dimethylsulfoxide (DMSO), ethyl acetate (AcOEt), dichloromethane (DCM), methylene chloride, pyridine, chloroform, acetonitrile (ACN or $CH_3CN$), dimethoxyethane, dioxane, tetrahydrofuran (THF) or mixtures thereof. More preferably, it is selected from N,N-dimethylacetamide (DMA), N-methylpyrrolidone (NMP) and N,N-dimethylformamide (DMF). The most preferably, the polar organic solvent is N,N-dimethylacetamide (DMA).

In the present invention, the coupling reaction is generally carried out at a temperature of greater than or equal to $-45°$ C. Often, the reaction is carried out at a temperature greater than or equal to $-25°$ C. Preferably, the temperature is greater than or equal to $-20°$ C. In the process according to the invention, the reaction is generally carried out at a temperature of less than or equal to $+45°$ C. Often, the reaction is carried out at a temperature of less than or equal to $+5°$ C. Preferably, the temperature is less than or equal to $0°$ C.

In another particular aspect of the present invention, the solution, which is generally the solution in which a coupling has taken place, can suitably be treated after the coupling step with an aqueous phase so as to provide a solution of coupled product in the aqueous phase and then, the coupled product is extracted from the aqueous phase into an organic solvent. In this case, the pH value of the aqueous phase is preferably controlled to be greater than or equal to 1. More preferably, it is greater than or equal to 1.5. Still more preferably, it is greater than or equal to 2. On the other hand, the pH value of the aqueous phase is preferably controlled to be less than or equal to 9. In some embodiments this pH value is preferably controlled to be less than or equal to 5. More preferably, in this embodiment, it is less than or equal to 3.5. Still more preferably, it is less than or equal to 3. Excellent results were obtained with a pH value of the aqueous phase of about 2.5.

It has been found that in the process according to the invention it is possible by carrying out washing operations at a pH as contemplated above, to eliminate acidic or basic impurities while maintaining high product quality of coupled product in particular with regard to sensitive groups such as the Gln moiety or protective groups optionally required for further coupling steps such as Boc or tBu group.

In still another particular aspect of the present invention, the solution, which is generally the solution in which the coupling has taken place, in particular to produce, in particular protected, X-Gly-Gly-Val-Leu-Val-Gln-Pro-Gly-Y octapeptide (SEQ ID NO 5), may be directly poured into an aqueous solvent in order to precipitate the desired product. In another embodiment, an aqueous solvent may be added to the solution in particular of protected X-Gly-Gly-Val-Leu-Val-Gln-Pro-Gly-Y octapeptide (SEQ ID NO 5) in order to crystallize the desired product. Such aqueous solvent may be, for example, water, salt water or any other aqueous mineral salt solution. The water pH value is preferably greater than or equal to 1.5, more preferably, greater than or equal to 2. On the other hand, the pH value of the aqueous phase is preferably controlled to be less than or equal to 10. More preferably, it is less than or equal to 9. Still more preferably, less than or equal to 8. Suitable salts to be used in above mentioned salt water solutions include alkali or earth alkali chlorides, in particular sodium chloride alkali or earth alkali sulphates, in particular potassium sulphate alkali or earth alkali hydrogenocarbonates, in particular sodium hydrogenocarbonate. A preferred aqueous phase consists of deionized water.

In a preferred embodiment Boc-Gly-Gly-Val-Leu-Val-Gln-Pro-Gly-OtBu octapeptide (SEQ ID NO 6) is obtained by coupling. In some embodiments, an amide type solvent, more preferably in DMA, and an aqueous phase, preferably comprising or consisting of water, such as deionized water, in particular GMP quality water having controlled quality, having a pH of about 7 is added to the solution of the protected peptide. The aqueous phase has generally a temperature of from 20'C to 70'C, preferably from 40° C. to 50° C.

In another embodiment, the organic solution of Boc-Gly-Gly-Val-Leu-Val-Gln-Pro-Gly-OtBu octapeptide (SEQ ID NO 6) is added to the aqueous phase.

It has been found that this preferred embodiment allows for particularly high purity and easy separation of the protected peptide which can be isolated in high yield as a purified solid.

Usually, the reaction product after the coupling step contains one or more protecting group(s). An example of such coupling product is a peptide derivative of formula X-Gly-Gly-Val-Leu-Val-Gln-Pro-Gly-Y (SEQ ID NO 5), wherein X and Y are as defined above. If desirable, the protecting groups can be removed, for example in a selective way. Thus it is possible to remove only certain protecting groups, keeping others intact during the subsequent reaction(s).

In a preferred aspect of the process according to the invention, the peptide derivative of formula X-Gly-Gly-Val-Leu-Val-Gln-Pro-Gly-Y (SEQ ID NO 5) is further deprotected of the amino protecting group X and of the acid protecting group Y to provide the free Gly-Gly-Val-Leu-Val-Gln-Pro-Gly octapeptide (SEQ ID NO 1).

In a particular aspect of the invention, a deprotection process is provided which comprises deprotecting at least the amino protecting group X in the peptide derivative of formula X-Gly-Gly-Val-Leu-Val-Gln-Pro-Gly-Y (SEQ ID NO 5) wherein Y is an optional protecting group for the carboxyl function. Preferably Y is a free carboxyl group or an acid labile carboxyl protecting group, for example, a tert.Butyl ester. In this embodiment, X is preferably an acid labile protecting group, in particular a Boc group. Deprotection can be carried out by means of an organic acid or a mineral acid. The organic acid can for example be selected from trifluoroacetic acid (TFA), trifluoromethylsulfonic acid, formic acid, p-toluene sulfonic acid and methanesulphonic acid. Deprotection is preferably carried out by means of a mineral acid, in particular HCl, preferably dissolved in an organic solvent. Good results are obtained by providing a solution of the amino protected peptide in a solvent comprising a carboxylic acid, preferably glacial acetic acid and adding a solution of mineral acid, preferably HCl in a polar organic solvent. In a first embodiment, the solution of the amino protected peptide is provided by adding organic solvent to a solution of the peptide in another solvent, for example, a workup solution from a coupling step. In a second embodiment, the amino protected peptide is in a first step precipitated or crystallized, filtrated and optionally washed and, in a second step, dissolved in the solvent, for example in glacial acetic acid. Ethers, in particular dioxane can also be used as polar organic solvent or co-solvent. The deprotection step is generally carried out at a temperature of from 0° C. to about 45° C., preferably from 30° C. to less than about 45° C., most preferably about 30° C. Generally, the reaction medium of the deprotection step is substantially anhydrous, containing less than 2% by weight relative to the total weight of the reaction medium of water. Preferably this content is equal to or less than 1% wt, in particular equal to or less than 0.5% wt.

In a preferred embodiment Boc-Gly-Gly-Val-Leu-Val-Gln-Pro-Gly-OtBu octapeptide (SEQ ID NO 6) which is preferably obtained by crystallization as described above, is dissolved in a solvent comprising or, preferably, consisting of glacial acetic acid. A solution of HCl in glacial acetic acid is added and deprotection is carried out at a temperature as described here before. In this most preferred embodiment, generally from 3 to 12 equivalents of HCl per molecule of protected peptide are used, preferably, from 5 to 10, more preferably from 6 to 8 equivalents of HCl per molecule of protected peptide are used. Using about 7 equivalents of HCl per molecule of protected peptide is more particularly preferred. In this preferred embodiment, the reaction medium of the deprotection reaction is preferably substantially anhydrous as described above.

It has been found that in particular the preferred embodiment here before allows for efficient deprotection while avoiding potential desamidation of Gln moiety and providing a solid deprotected peptide salt which can be recovered easily from the reaction medium of the deprotection step.

In the process according to the invention, at least one peptide coupling step is carried out in solution. Preferably, at least 2, for example 2, 3 or 4 and more preferably at least 5 peptide coupling steps for example 5, 6 or 7 coupling steps are carried out in solution. Still more preferably, all coupling steps are carried out in solution. Particular solution phase coupling steps which are useful in the process according to the invention are apparent from the synthesis in the schemes hereafter.

A first synthetic approach is detailed in the scheme 1 shown in FIG. 1.

Figure 2:
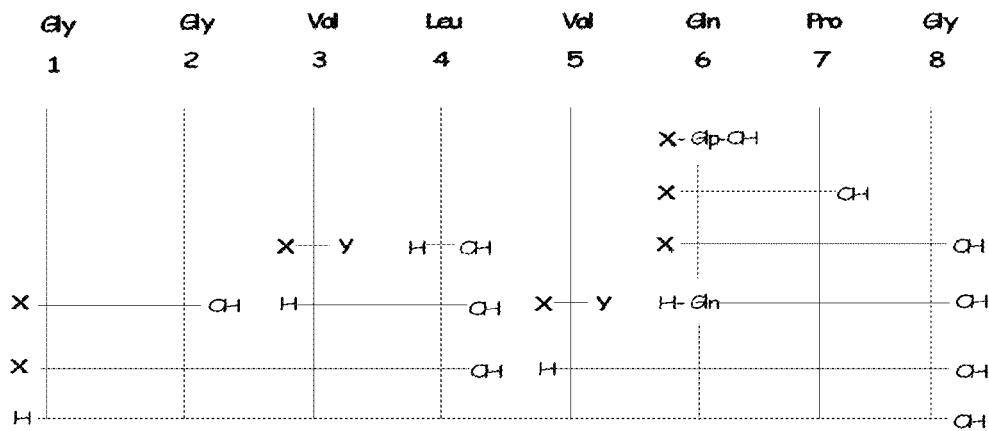
FIG. 2 illustrates scheme 2, which is an embodiment of scheme 1 for synthesizing the octapeptide of SEQ ID NO 1.

A particular embodiment of the process according to scheme 1 is in accordance with scheme 2, shown in FIG. 2.

Good results were obtained when the fragments 3-4, 6-7, 6-8 and 5-8 of scheme 1 or 2 were under their persilylated form. In another preferred embodiment, the 8-Gly in scheme 1 is protected as carboxylic ester, in particular a tert.-butyl ester.

Figure 3:
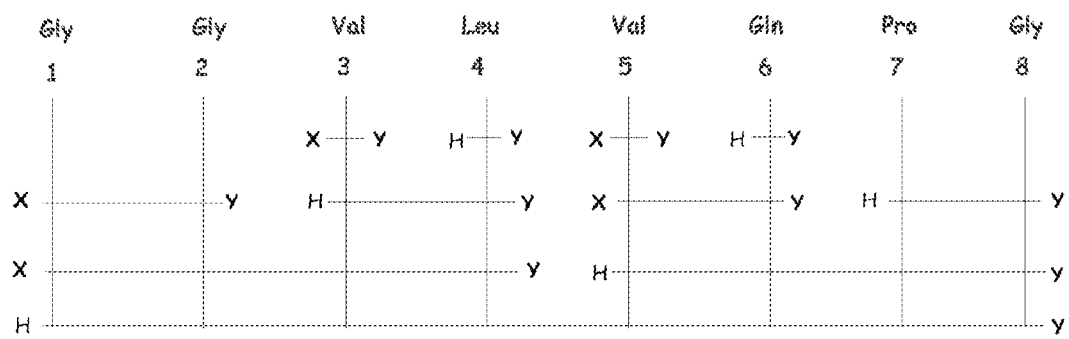
FIG. 3 illustrates a scheme 3 for synthesizing the octapeptide of SEQ ID NO 1.

A further synthetic approach is detailed in scheme 3 shown in FIG. 3, wherein X and Y are as generally defined above. Good results are obtained when the 8-Gly in scheme 2 is protected as carboxylic ester, in particular as tert.-butyl ester.

In the process according to the invention, the pressure in the solution phase coupling step is generally chosen so as to maintain the solution in the liquid state. Atmospheric pressure (approximately 101.3 kPa) and superatmospheric pressures are very suitable.

The reaction products can be isolated and purified by purification methods, such as for example extraction, crystallization, lyophilisation, spray-drying, precipitation or chromatography (e.g. thin layer or column). Isolation and purification by precipitation or crystallization is preferred. In one embodiment, at least one intermediate peptide or the final product is isolated and purified by precipitation or crystallization. In a particularly preferred embodiment of the process according to the invention, all intermediates and final products are isolated and purified, if desired, by precipitation or crystallization. Intermediates and the end products may, for example, be characterized by chromatographic parameters (purity control), optical rotation and possibly spectroscopic data.

The X-Val-Gln-Pro-Gly peptide (SEQ ID NO 7) may be obtained by various synthetic approaches. Excellent results were obtained with the two approaches below, namely the 1+3 and the 2+2 approaches.

In still another particular aspect of the present invention, the process as above described may comprise the manufacture of X-Val-Gln-Pro-Gly peptide (SEQ ID NO 7) wherein X is an amino protecting group as described above by coupling of X-Val with Gln-Pro-Gly peptide (1+3 approach).

Such tetrapeptide manufacture preferably comprises activating the carboxylic acid function of X-Val e.g. in an activated ester form of the X-Val, preferably with N-hydroxysuccinimide. In particular, X may be benzyloxycarbonyl (Z).

In still another particular aspect of the present invention, the process as above described may comprise the manufacture of X-Val-Gln-Pro-Gly peptide (SEQ ID NO 7) wherein X is an amino protecting group as described above by coupling of X-Val-Gln with Pro-Gly peptide (2+2 approach).

The X-Val-Gln dipeptide is preferably obtained by the activation of the carboxylic acid function of X-Val e.g. in an activated ester form of the X-Val, preferably with N-hydroxysuccinimide. In particular, X may be benzyloxycarbonyl (Z). On the other hand, the X-Pro-Gly-Y is preferably obtained by the reaction between X-Pro with Gly-Y, wherein X is preferably a benzyloxycarbonyl (Z) group and Y is preferably a tert-butyl ester. Such reaction may be performed under classical activation conditions as above described, in particular by using carbodiimides and N-hydroxysuccinimide reagents.

The obtained X-Pro-Gly-Y peptide may be deprotected from its X group by acidolysis, hydrogenolysis, treatment with dilute ammonium hydroxide, treatment with sodium, treatment with sodium amide, treatment with hydrazine, or enzymatic hydrolysis. It is preferably removed by hydrogenolysis.

The coupling between the X-Val-Gln and Pro-Gly-Y may be also performed under various conditions. Carbonyl halide, more particularly acyl halide, in particular acyl chloride coupling agents as described above are preferred. Acyl halide, in particular acyl chloride coupling agents as described above are preferred. Tertiary acyl halides are more particularly preferred. Examples of tertiary acyl halides are inter alia 1-adamantoyl chloride, 2,2-dimethylbutyroyl chloride and pivaloyl chloride. Excellent results were obtained while using pivaloyl chloride, isobutyl chloroformate is also a very suitable coupling agent.

It has been found that it is possible, in particular, by carefully selecting the carboxylic acid activating agent and in particular with tertiary acyl halides to substantially or completely avoid racemisation, in particular of any Gln group when coupling X-Val-Gln or Pro-Gly-Y fragments as described herein before. More particularly, it is possible to substantially avoid undesired side-reactions on the side chain of Gln and of the Pro moiety. Moreover coupling conditions have been identified which are described here after, which allow for high overall high productivity and yield in particular of desired tetrapeptide while maintaining excellent optical purity.

The above described couplings are generally carried out at a temperature of greater than or equal to −30° C. Often, the reaction is carried out at a temperature greater than or equal to −10° C. Preferably, the temperature is greater than or equal to −5° C. This reaction is generally carried out at a temperature of less than or equal to +45° C. Often, the reaction is carried out at a temperature of less than or equal to +30° C. Preferably, the temperature is less than or equal to +25° C.

The above described couplings are preferably carried out in solution. In this case, the pressure is chosen so as to maintain the solution in the liquid state. Atmospheric pressure (approximately 101.3 kPa) and superatmospheric pressures are very suitable. When this coupling according to the present invention is carried out in solution, said solution may suitably comprise acetonitrile (ChhCN) and/or an aqueous medium.

In another embodiment, this coupling is carried out in an organic solvent which is preferably chosen from alkyl ester solvents such as ethyl acetate (AcOEt), chlorinated solvents such as dichloromethane (DCM), and amide-type solvents such as N,N-dimethylacetamide (DMA) and N,N-dimethylformamide (DMF). In this embodiment, in particular when an amide type solvent is used, it is possible to use the tetrapeptide solution after optional separation, in particular filtration of optionally present solids such as hydrogenation catalyst, without isolation of the tetrapeptide in a further coupling step as described above, in particular in accordance with scheme 2 or 3.

The reaction medium may then be suitably treated after the coupling step with an aqueous phase so as to provide a solution of coupled product in the aqueous phase and then, the X-Val-Gln-Pro-Gly-Y peptide (SEQ ID NO 8) is extracted from the aqueous phase into an organic solvent.

The intermediate fragments and the X-Val-Gln-Pro-Gly-Y peptide (SEQ ID NO 8) may be recovered by precipitation and/or crystallization. In some cases, the X-Val-Gln-Pro-Gly-Y peptide (SEQ ID NO 8) is generally provided as solution in a first solvent and then precipitated by addition to a second solvent wherein the peptide is less soluble than in the first solvent. In other cases, the X-Val-Gln-Pro-Gly-Y peptide (SEQ ID NO 8) is generally provided as solution in a first solvent and then crystallized by the addition of a second solvent wherein the peptide is less soluble than in the first solvent.

The first solvent is advantageously selected from the group consisting of ethyl acetate, tetrahydrofuran, dichloromethane, dioxane, methanol, n-butanol, isobutanol, 2-butanol, 2-propanol, diisopropyl ether, diethyl ether, methylterbutylether, N,N-dimethylacetamide (DMA), N,N-dimethylformamide (DMF), and mixtures thereof. Good results were obtained with a dichloromethane/isobutanol mixture.

The second solvent advantageously comprises at least one solvent chosen from water, diisopropyl ether, acetonitrile, diethyl ether, methylterbutylether, ethyl acetate, isopropyl acetate, acetone, tetrahydrofuran, dichloromethane or dioxane. Good results were obtained with diisopropyl ether.

In still another particular aspect of the present invention, the process as above described may comprise the manufacture of Val-Gln-Pro-Gly tetrapeptide (SEQ ID NO 4), wherein the manufacture of the X-Val-Gln-Pro-Gly-Y (SEQ ID NO 8) peptide further comprises the deprotection of the N-terminal amino protecting group X. In particular, X may be benzyloxycarbonyl (Z).

Such amino protecting groups X may be removed by acidolysis, hydrogenolysis, treatment with dilute ammonium hydroxide, treatment with sodium, treatment with sodium amide, treatment with hydrazine, or enzymatic hydrolysis. It is preferably removed by hydrogenolysis.

In still another particular aspect of the present invention, the process as above described comprises in addition the manufacture of X-Gln-Pro-Gly-Y tripeptide, wherein X is an amino protecting group, by ring opening of X-Glp-Pro-Gly-Y tripeptide with ammonia.

In still another particular aspect of the present invention, the process as above described comprises in addition the manufacture of Gly-Gly-Val-Leu tetrapeptide (SEQ ID NO 9) by coupling of Val-Leu dipeptide with X-Gly-Gly or X-Gly. Generally, this coupling is carried out in the presence of a carboxylic acid activating agent. In one embodiment, carbodiimides, acyl halides, phosphonium salts and uronium or guanidinium salts are generally preferred as carboxylic acid activating agent. Carbonyl halide, more particularly acyl halide, in particular acyl chloride coupling agents as described above are preferred. Tertiary acyl halides are more particularly preferred. Examples of tertiary acyl halides are inter alia 1-adamantoyl chloride, 2,2-dimethylbutyroyl chloride and pivaloyl chloride. More preferably, the coupling agent is chosen from isobutyl chloroformate and pivaloyl-chloride.

In another embodiment, the coupling is preferably carried out with an activated ester form of the X-Gly-Gly, preferably with N-hydroxysuccinimide.

When acyl halides are used as carboxylic acid activating agents, this coupling is generally carried out in the presence of a base as additional reagent. It is preferably chosen from N-methylmorpholine (NMM), pyridine, diisopropylethylamine (DIPEA) or triethylamine (TEA). More preferably it is N-methylmorpholine (NMM).

The coupling of a Val-Leu dipeptide with X-Gly-Gly or X-Gly is preferably carried out in solution. In this case, the pressure is chosen so as to maintain the solution in the liquid state. Atmospheric pressure (approximately 101.3 kPa) and superatmospheric pressures are very suitable. The solution generally comprises a polar organic solvent. Preferably, the polar organic solvent is selected from N,N-dimethylacetamide, N,N-dimethylformamide, N-methylpyrrolidone, dimethylsulfoxide, ethyl acetate, dichloromethane or mixtures thereof. More preferably, the solution comprises N,N-dimethylacetamide or ethyl acetate.

The Glycine amino acid or dipeptide Gly-Gly is generally protected by an amino protecting group X. The amino protecting group X is preferably selected from tert-butyloxycarbonyl, benzyloxycarbonyl, 9-fluorenylmethyloxycarbonyl, 2-nitrobenzenesulfonyl, 2-nitrobenzenesulfenyl, and substituted derivatives. More preferably, the amino protecting group X is tert-butyloxycarbonyl (BOC).

The Val-Leu dipeptide is generally protected by a carboxylic acid protecting group Y.

Preferred carboxylic acid protecting group Y are alkyl, aryl and silylated derivatives. In a particularly preferred variant, the Val-Leu peptide derivative is a persilylated derivative. The persilylation of Val-Leu dipeptide can be carried out, for example, according to the method described in Patent Application EP-A-184243. It is preferably carried out with MSA.

The coupling of a Val-Leu dipeptide with a X-Gly-Gly or X-Gly is generally carried out at a temperature of greater than or equal to −45° C. Often, the reaction is carried out at a temperature greater than or equal to −25° C. Preferably, the temperature is greater than or equal to −20° C. In the method according to the invention, the coupling is generally carried out at a temperature of less than or equal to +45° C. Often, this reaction is carried out at a temperature of less than or equal to +5° C. Preferably, the temperature is less than or equal to 0° C.

The tetrapeptide obtained as above described may be further deprotected of the amino protecting group X and of the acid protecting group Y to provide the free Gly-Gly-Val-Leu tetrapeptide (SEQ ID NO 9).

The reaction products can then be isolated and purified by purification methods, such as for example extraction, crystallization, lyophilisation, spray-drying, precipitation or chromatography (e.g. thin layer or column).

The coupling steps as above described of the present invention may be carried out under persilylation conditions. In other words, the amino acids or peptides used in the process according to the present invention may be protected under their persilylated form. They are preferably protected under their persilylated form.

Another aspect of the present invention is related to a tripeptide of the formula Glp-Pro-Gly or protected peptide of the formula X-Glp-Pro-Gly, wherein X is an amino protecting group, or protected peptide of the formula X-Glp-Pro-Gly-Y, wherein X is an amino protecting group and Y is a carboxylic acid protecting group, to a tripeptide of the formula Gln-Pro-Gly or protected peptide of the formula X-Gln-Pro-Gly, wherein X is an amino protecting group, to a tetrapeptide of the formula Val-Gln-Pro-Gly (SEQ ID NO 4) or protected peptide of the formula X-Val-Gln-Pro-Gly (SEQ ID NO 7), wherein X is an amino protecting group and in particular when X is benzyloxycarbonyl, to a pentapeptide of the formula Leu-Val-Gln-Pro-Gly (SEQ ID NO 10), to an hexapeptide of the formula Val-Leu-Val-Gln-Pro-Gly (SEQ ID NO 11) and to an heptapeptide of the formula Gly-Val-Leu-Val-Gln-Pro-Gly (SEQ ID NO 12), which may be obtained, as such or under their protected form, as intermediates during a process according to the present invention.

Besides, the present invention also relates to a dodecapeptide of the formula Gly-Gly-Val-Leu-Val-Gln-Pro-Gly-Val-Gln-Pro-Gly (SEQ ID NO 13), to an hexakaidecapeptide of the formula Gly-Gly-Val-Leu-Val-Gln-Pro-Gly-Gly-Gly-Val-Leu-Val-Gln-Pro-Gly (SEQ ID NO 14) and to a modified peptide of the formula $CH_3C(=O)$—NH-Gly-Gly-Val-Leu-Val-Gln-Pro-Gly (SEQ ID NO 15), which may be obtained during a process according to the present invention.

The present invention also relates to the use of the following peptides as intermediates in peptide synthesis: Tripeptide of the formula Glp-Pro-Gly; Tetrapeptide of the formula Val-Gln-Pro-Gly (SEQ ID NO 7); pentapeptide of the formula Leu-Val-Gln-Pro-Gly (SEQ ID NO 10); hexapeptide of the formula Val-Leu-Val-Gln-Pro-Gly (SEQ ID NO 11); heptapeptide of the formula Gly-Val-Leu-Val-Gln-Pro-Gly (SEQ ID NO 12), as such or under their protected form.

One of the major issues in peptide synthesis is related to the isolation and purification of the peptides, which are often the cause of a reduction in the yield of the final peptide product.

In consequence, the invention also relates to the purification of the above described peptides, as such or under their protected form. The purification according to the invention allows in particular meeting specifications concerning purification related to organic impurities such as for example organic solvents, such as acetonitrile and is industrializable.

The purification process according to the present invention allows an efficient and low cost production of said purified octapeptide.

It is thus also an object of the present invention to provide a process for the purification of Gly-Gly-Val-Leu-Val-Gln-Pro-Gly peptide (SEQ ID NO 1) or anyone of the peptides of the formula Val-Gln-Pro-Gly (SEQ ID NO 4) or X-Val-Gln-Pro-Gly (SEQ ID NO 7), wherein X is an amino protecting group, Leu-Val-Gln-Pro-Gly (SEQ ID NO 10), Val-Leu-Val-Gln-Pro-Gly (SEQ ID NO 11), Gly-Val-Leu-Val-Gln-Pro-Gly (SEQ ID NO 12), Gly-Gly-Val-Leu-Val-Gln-Pro-Gly-Val-Gln-Pro-Gly (SEQ ID NO 13), Gly-Gly-Val-Leu-Val-Gln-Pro-Gly-Gly-Gly-Val-Leu-Val-Gln-Pro-Gly (SEQ ID NO 14), and $CH_3C(=O)$—NH-Gly-Gly-Val-Leu-Val-Gln-Pro-Gly (SEQ ID NO 15), as such or under a protected form wherein the peptide is dissolved in a first solvent and then precipitated or crystallized. The precipitation is performed by the addition of the solution of the peptide in the first solvent into a second solvent wherein the peptide is less soluble than in the first solvent. The crystallization is performed by the addition to the solution of the peptide in the first solvent of a second solvent wherein the peptide is less soluble than in the first solvent.

The peptide may be dissolved by the addition of a first solvent or may be directly obtained after the work-up as a solution in a first solvent. In this latter case, the solution may be concentrated under vacuum before the addition of the second solvent.

The nature of the first and second solvent depends on the nature of the peptide, on its isoelectric point value and on its protected or unprotected form. The peptide should be more soluble in the first solvent than in the second solvent.

In one aspect, when the peptide is unprotected, the first solvent is preferably an aqueous medium and the second solvent preferably comprises at least one polar organic solvent. The pH of the aqueous medium may in some cases preferably be controlled. On the other hand, in the case of a protected peptide, the first solvent comprises preferably at least one polar organic solvent while the second solvent is preferably an aqueous medium.

The organic solvent is preferably chosen from isopropyl ether (IPE), acetonitrile ($CH_3CN$), methylterbutylether (MTBE), ethyl acetate (AcOEt), isopropyl acetate (AcOiPr), acetone, tetrahydrofurane (THF), dichloromethane (DCM), dioxane, methanol, tert-butanol, isopropanol, ethanol, acetic acid, N,N-dimethylacetamide (DMA), N,N-dimethylformamide (DMF) and the like or mixtures thereof. Good results were obtained with isopropyl ether and/or acetonitrile.

In one particular aspect, a polar organic solvent, preferably selected from acetonitrile (CH3CN), ethyl acetate (AcOEt), isopropyl acetate (AcOiPr), acetone, tetrahydrofurane (THF), dichloromethane (DCM), dioxane, methanol, tert-butanol, isopropanol, ethanol, acetic acid, N,N-dimethylacetamide (DMA), N,N dimethylformamide (DMF) and the like or mixtures thereof.

Tables 1 and 2 give exemplary combinations of first and second solvents for the different fragments.

TABLE 1

Solvent Combinations

| Peptide | First solvent | Second solvent |
| --- | --- | --- |
| H-Val-Leu-OH | methanol/water | isopropanol |
| Z-Glp-Pro-OH | water/acetonitrile | water |
| Z-Glp-Pro-Gly-OH | water/dichloromethane | Aqueous $KHSO_4$ solution |
| H-Gln-Pro-Gly-OH | water | ethanol |
| Z-Val-Gln-Pro-Gly-OH (SEQ ID NO 16) | Isobutanol/dichloromethane | diisopropylether |
| H-Val-Gln-Pro-Gly-OH (SEQ ID NO 4) | methanol | acetonitrile |
| HCl-H-Gly-Gly-Val-Leu-Val-Gln-Pro-Gly-OH (SEQ ID NO 1) | Acetic acid/dioxane | diisopropylether |
| CH3COO-H-Gly-Gly-Val-Leu-Val-Gln-Pro-Gly-OH (SEQ ID NO 1) | Ammonium acetate aqueous buffer | acetonitrile |

TABLE 2

Alternative Solvent Combinations

| Peptide | First solvent | Second solvent |
| --- | --- | --- |
| H-Val-Leu-OH | isopropanol/water | isopropanol |
| Boc-Gly-Gly-Val-Leu-OH (SEQ ID NO: 17) | ACOEt | diisopropylether |
| Z-Val-Gln-OH | Isobutanol | AcOiPr |
| H-Val-Gln-Pro-Gly-OtBu (SEQ ID NO 18) | ACOEt | diisopropylether |
| Boc-Gly-Gly-Val-Leu-Val-Gln-Pro-Gly-OtBu (SEQ ID NO 19) | DMA | water |
| HCl-H-Gly-Gly-Val-Leu-Val-Gln-Pro-Gly-OH (SEQ ID NO 1) | Acetic acid/dioxane | MeCN/diisopropylether |
| CH3COO-H-Gly-Gly-Val-Leu-Val-Gln-Pro-Gly-OH (SEQ ID NO 1) | Ammonium acetate aqueous buffer | EtOH |

It may be advantageous to isolate and purify the desired peptide product by salt formation (e.g. hydrochloride, acetate, dicyclohexyl ammonium, cyclohexyl ammonium or trifluoroacetate salt formation) or by zwitterion formation. As used herein, particularly with reference to the peptide having the amino acid sequence Gly-Gly-Val-Leu-Val-Gln-Pro-Gly (SEQ ID NO 1), the term "salt(s) of the peptide" includes and encompasses stoichiometric and non-stoichiometric salts. As stated above, these salts may also have associated water molecules (hydrates) and may further be crystalline materials.

The peptide can also be separated from a solution for example by spray-drying, filtration or decantation and dried before optionally being submitted to further processing steps such as combining with other ingredients, lyophilization, spray-drying, packaging and/or storage.

According to one suitable approach, the peptide is collected via filtering and optionally washed, in particular to reduce possible salt content, and then dried.

A further particular aspect of the present invention is related to a process for purifying Gly-Gly-Val-Leu-Val-Gln-Pro-Gly peptide (SEQ ID NO 1), or anyone of the peptides of the formula Val-Gln-Pro-Gly (SEQ ID NO 4) or X-Val-Gln-Pro-Gly (SEQ ID NO 7), wherein X is an amino protecting group, Leu-Val-Gln-Pro-Gly (SEQ ID NO 10), Val-Leu-Val-Gln-Pro-Gly (SEQ ID NO 11), Gly-Val-Leu-Val-Gln-Pro-Gly (SEQ ID NO 12), Gly-Gly-Val-Leu-Val-Gln-Pro-Gly-Val-Gln-Pro-Gly (SEQ ID NO 13), Gly-Gly-Val-Leu-Val-Gln-Pro-Gly-Gly-Gly-Val-Leu-Val-Gln-Pro-Gly (SEQ ID NO 14), and $CH_3C(=O)$—NH-Gly-Gly-Val-Leu-Val-Gln-Pro-Gly (SEQ ID NO 15) as such or under a protected form, which comprises subjecting a crude peptide of any of the aforesaid sequences to a chromatography operation.

In the present invention, the chromatography is preferably chosen from medium pressure liquid chromatography (MPLC) and high pressure liquid chromatography (HPLC).

In this aspect, the chromatography operation may take place prior or after an optional precipitation or crystallization of the peptide.

The chromatography operation may be processed for example on columns with a continuous bed (monolithic columns). In that case, normal phase stationary phases can be used, for example silica or alumina. In that case apolar mobile phases are generally used. Reverse phase stationary phases such as hydrophobically modified inorganic supports, typically silica grafted with organic hydrophobic compounds are preferably used. In that case polar mobile phases are generally used, for example aqueous mobile phases containing an organic co-solvent, in particular a polar organic co-solvent, such as methanol, ethanol, isopropanol, acetonitrile or dioxane. Medium polar such as silica with bonded diol, propyl-cyano or amino groups may also be used in particular with moderately polar mobile phases such as buffered aqueous/organic mobile phases.

The chromatography operation may be a medium pressure liquid chromatography (MPLC). In such a chromatography operation, the eluent may comprise water, acetonitrile ($CH_3CN$), alcohols such as methanol, ethanol, propanol and the like. Preferably, it comprises water ($H_2O$) and/or acetonitrile ($CH_3CN$). The eluent may also comprise a certain amount of salts to maintain its pH value to a certain area (buffer solution). Good results were obtained when an aqueous solution of ammonium acetate was used as eluent.

A further particular aspect of the present invention is related to a solution of Gly-Gly-Val-Leu-Val-Gln-Pro-Gly peptide (SEQ ID NO 1) or anyone of the peptides of the formula Val-Gln-Pro-Gly (SEQ ID NO 4) or X-Val-Gln-Pro-Gly (SEQ ID NO 7), wherein X is an amino protecting group, Leu-Val-Gln-Pro-Gly (SEQ ID NO 10), Val-Leu-Val-Gln-Pro-Gly (SEQ ID NO 11), Gly-Val-Leu-Val-Gln-Pro-Gly (SEQ ID NO 12), Gly-Gly-Val-Leu-Val-Gln-Pro-Gly-Val-Gln-Pro-Gly (SEQ ID NO 13), Gly-Gly-Val-Leu-Val-Gln-Pro-Gly-Gly-Gly-Val-Leu-Val-Gln-Pro-Gly (SEQ ID NO 14), and $CH_3C(=O)$—NH-Gly-Gly-Val-Leu-Val-Gln-Pro-Gly (SEQ ID NO 15), as such or under a protected form, in a solvent mixture comprising water and a polar organic solvent.

The above described solution according to the invention preferably comprises acetonitrile and alcohols such as methanol, ethanol, propanol and the like. Such solution may be used in a purification operation.

Another preferred aspect of the present invention is related to providing acetate-containing Gly-Gly-Val-Leu-Val-Gln-Pro-Gly octapeptide (SEQ ID NO 1) having different acetate content. It has been found that, depending on the isolation method used, different molar contents of acetate in the final peptide can be achieved, which may present certain advantages as to their stability. It should be understood that the present invention includes stoichiometric and non-stoichiometric salts of the peptide having the amino acid sequence Gly-Gly-Val-Leu-Val-Gln-Pro-Gly (SEQ ID NO 1) and that the general terms "salt(s)" and "salt(s) of the peptide" are to be understood as referring to and including stoichiometric and non-stoichiometric salts. It should also be understood that the phrase "acetate containing peptide" also refers to and includes stoichiometric and non-stoichiometric acetate salts. In addition, as used herein, the peptide (or octapeptide) having the sequence Gly-Gly-Val-Leu-Val-Gln-Pro-Gly (SEQ ID NO 1) may also be referred to by the USAN/INN name "larazotide". It has also been found that, depending on the isolation method used, the acetate salt of the peptide may have varying amounts of water also associated with it; thus these acetate salts can be classified as (stoichiometric as well as non-stoichiometric) hydrates (or "hydrated acetate salts"). As used herein, unless expressly stated to the contrary, the terms "larazotide acetate" or "acetate-containing peptide" or "acetate-containing octapeptide" refers to all solid state forms of the acetate-containing peptide having the sequence Gly-Gly-Val-Leu-Val-Gln-Pro-Gly (SEQ ID NO 1) irrespective of the amounts of acetate and/or water associated with the peptide.

In a first embodiment, the acetate-containing peptide is isolated from an aqueous peptidic solution by lyophilization. Lyophilization is intended to denote a means of drying a desired substance, achieved by freezing an aqueous medium containing said substance and causing ice to sublime directly to vapor by exposing it to a low partial pressure of water vapor. In this case, the acetate-containing peptide has generally a concentration of acetate of at least or equal to 60 mol %/mole of peptide.

In a second embodiment, the acetate-containing peptide is precipitated from the liquid medium by concentrating the liquid medium e.g. by evaporation. In this case, the acetate-containing peptide has generally a concentration of acetate of from 30 mol % to 60 mol % preferably about 50 mol %/mole of peptide. A suitable starting solution can be obtained, for example, by chromatography, in particular MPLC, of a crude product obtained from a deprotection step as described above. For example, a crude product obtained in particular by deprotection with HCl can be subjected to a chromatography operation in particular as described above. The solution containing acetate-containing peptide and a polar organic solvent, in particular acetonitrile, which solution is obtained from the chromatography operation can be concentrated for example by evaporation, preferably under reduced pressure, preferably at a temperature of from 20 to 50° C. As the solution is concentrated, acetate-containing peptide starts to precipitate and may be recovered by filtration. Precipitation efficiency may be enhanced, for example by cooling down the concentrated solution, typically to a temperature below 10° C.

In a third embodiment, the acetate-containing peptide is crystallized from the liquid medium by exchanging the chloride counter-ion of the chloride salt of the octapeptide Gly-Gly-Val-Leu-Val-Gln-Pro-Gly (SEQ ID NO 1) by an acetate ion. In this case, the acetate-containing peptide (larazotide acetate) has generally a concentration of acetate from more than 0 to less than 50 mole %/mole of peptide, preferably from 20 to 30 mole %/mole of peptide. In another embodiment, the acetate-containing octapeptide Gly-Gly-Val-Leu-Val-Gln-Pro-Gly (SEQ ID NO 1) is crystalline and comprises less than about 20 mole % acetate. In still another embodiment, the acetate-containing octapeptide Gly-Gly-Val-Leu-Val-Gln-Pro-Gly (SEQ ID NO 1) is crystalline and comprises less than about 15 mole % of acetate. In a yet further embodiment, the acetate-containing octapeptide Gly-Gly-Val-Leu-Val-Gln-Pro-Gly (SEQ ID NO 1) is crystalline and comprises less than about 10 mole % of acetate, preferably between about 4 to about 8 mol % of acetate. It should be understood that any of the foregoing references to crystalline acetate-containing octapeptide Gly-Gly-Val-Leu-Val-Gln-Pro-Gly (SEQ ID NO 1) may further include associated water molecules, i.e., crystalline hydrated acetate salts of the peptide, as further described below.

In a particularly advantageous aspect, it is possible to crystallize the acetate-containing peptide by adding a source of acetate ions to a liquid medium obtained by dissolving chloride salt of the Gly-Gly-Val-Leu-Val-Gln-Pro-Gly octapeptide (SEQ ID NO 1) obtained from a deprotection step as described above in water. Suitable sources of acetate include acetate salts, for example sodium acetate, potassium acetate or ammonium acetate. Ammonium acetate has given good results. Preferably, the pH during crystallization is controlled in a range from 2.5 to 7.5. A pH of from 3.5 to 6.5 is more particularly preferred. A pH of about 4.5 has given good results. In this embodiment the initial concentration of the chloride salt of the Gly-Gly-Val-Leu-Val-Gln-Pro-Gly octapeptide (SEQ ID NO 1) determined as free peptide is generally from 2 to 20% wt relative, to the total weight of the liquid medium containing said chloride salt and the source of acetate ions, and, if necessary, the pH adjusting agent, for example a base such as ammonia, all preferably dissolved in water. Preferably, this initial concentration is from 10 to 15% by weight. The temperature during crystallization is generally from 5° C. to 35° C., preferably from 20° C. to 30° C.

In a fourth embodiment, it is possible to prepare an acetate-free peptide, preferably in zwitterionic form, by crystallizing from the liquid medium by adjusting the pH of an aqueous solution of the chloride salt of the Gly-Gly-Val-Leu-Val-Gln-Pro-Gly octapeptide (SEQ ID NO 1) to the isoelectric point of the peptide, which is about 6.0 to 7.0, more particularly about 6.5. When the free peptide is desired, it is preferred to avoid the presence of supplementary counter-ions such as acetate.

The invention also concerns said acetate-containing peptides. It has been found, surprisingly, that the stability of the peptide is improved when the acetate content is reduced and also on account of its manufacturing process. An acetate-containing peptide obtained by crystallization or precipitation as described above is more stable than a lyophilized peptide. It has also been found that the amount of water associated with the acetate-containing octapeptide Gly-Gly-Val-Leu-Val-Gln-Pro-Gly (SEQ ID No 1) also varies with the method of preparation. In one embodiment the acetate-containing octapeptide Gly-Gly-Val-Leu-Val-Gln-Pro-Gly (SEQ ID No 1) is crystalline and comprises less than about 7 mol % water. In another embodiment, the acetate-containing octapeptide Gly-Gly-Val-Leu-Val-Gln-Pro-Gly (SEQ ID No 1) is crystalline and comprises less than about 5 mol % water. In a further embodiment, the acetate-containing octapeptide Gly-Gly-Val-Leu-Val-Gln-Pro-Gly (SEQ ID No 1) is crystalline and comprises less than about 3 mol % water. In a yet further embodiment, the acetate-containing octapeptide Gly-Gly-Val-Leu-Val-Gln-Pro-Gly (SEQ ID No 1) is crystalline and comprises between about 1 mol % to about 2 mol % water.

The invention concerns also the manufacture of said acetate-containing peptides by the methods indicated.

The chloride salt introduced into a salt exchange step of the Gly-Gly-Val-Leu-Val-Gln-Pro-Gly octapeptide (SEQ ID NO 1) has preferably a purity of at least 98.5% by HPLC.

EXAMPLES

The following examples are intended to illustrate the invention without, however, limiting its scope.

In these examples and throughout this specification the abbreviations employed are defined as follows:

AcOH is acetic acid, AcOEt is ethyl acetate, AcOiPr is isopropyl acetate, Boc is t-butoxycarbonyl, n-BuOH is n-butanol, Cbz is benzyloxycarbonyl, DCC is 1,3 dicyclohexylcarbodiimide, DCM is dichloromethane, DIC is 1,3-diisopropylcarbodiimide, DIPEA is N,N-diisopropylethylamine, DMAPA is 3-dimethylaminopropylannine, DMF is N,N-dimethylformamide, DMA is N,N-dimethylacetamide, Fmoc is fluorenylmethyloxycarbonyl, HBTU is N,N,N',N'-tetramethyl-O-(1H-benzotriazol-1-yl)uronium-hexafluororphosphate), HOBT is 1-hydroxybenzotriazole, HOOBT is 3,4-dihydro-3-hydroxy-4-oxo-1,2,3-benzotriazine, HPW is high purity water IBCF is isobutyl chloroformate, PivCl is Pivaloyl chloride, i-BuOH is isobutanol, IPE is diisopropylether, MeCN or ACN is acetonitrile, MeOH is methanol, NMM is N-methylmorpholine, NMP is 1-methyl-2-pyrrolidone, THF is tetrahydrofuran, MSA is N-Methyl-N trimethylsilylacetamide, Tos is tosyl, MTBE is Methyl-tert-butylether.

Examples 1 to 11

Figure 4:
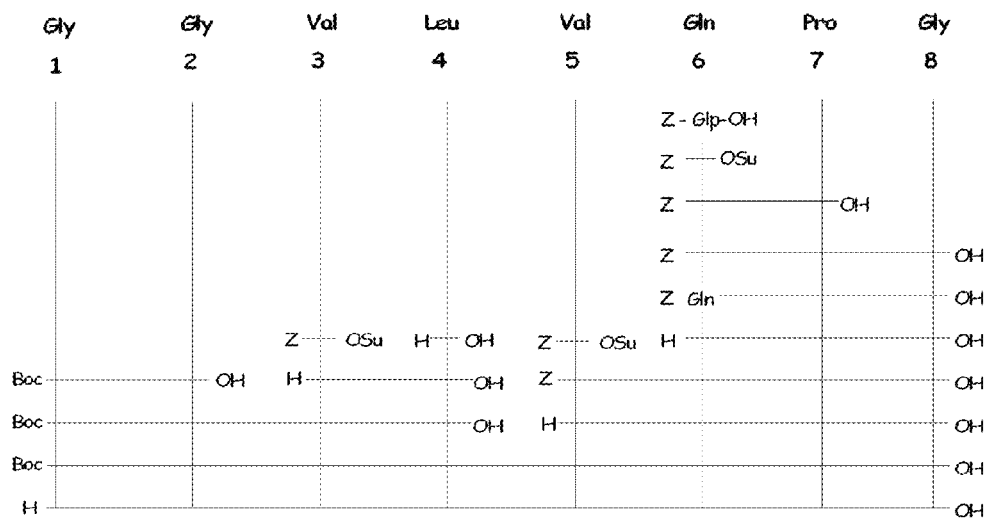
FIG. 4 illustrates a scheme 4 for synthesizing the octapeptide of SEQ ID NO 1.

Scheme 4 (FIG. 4) represents a first general synthetic approach of the Gly-Gly-Val-Leu-Val-Gln-Pro-Gly (SEQ ID NO 1) octapeptide which will be detailed in the following examples.

Example 1

Synthesis of H-Val-Leu-OH

Leucine (1.2 eq.) was silylated in pure MSA at maximum 50° C. until complete dissolution and then diluted with AcOEt. The leucine solution was transferred to a Z-Val-OSu solution under stirring at 35° C. The reaction was quenched with water, diluted with AcOEt and the organic phase was washed with $KHSO_4$ and NaCl. The solvent was removed under vacuum and replaced with MeOH. Water was then added to the methanolic solution followed by the addition of the palladium catalyst. The deprotection of the Z group took place with the introduction of gaseous hydrogen at 30° C. Once the reaction completed, the catalyst was filtrated and washed with a 50/50 mixture of methanol and water. The solvent was evaporated and the mixture diluted with isopropanol to precipitate the dipeptide. The dipeptide was then recovered by filtration, washed with isopropanol at room temperature and then dried. The dipeptide was isolated with a yield of 85%.

Example 2

Synthesis of H-Val-Leu-OH

Leucine (1.2 eq.) was silylated in pure MSA at at most 50° C. until complete dissolution and then diluted with AcOEt. The leucine solution was transferred to a Z-Val-OSu solution under stirring at 35° C. The unreacted ZValOSu was neutralized with DMAPA (0.05 eq.) and the reaction was quenched with water, diluted with AcOEt and the organic phase was washed with $KHSO_4$ and NaCl. The solvent was removed under vacuum and replaced with iPrOH until the AcOEt content in the evaporates was <5% weight. Water was then added to the peptidic solution followed by the addition of the palladium catalyst. The deprotection of the Z group took place with the introduction of gaseous hydrogen at about 35° C. Once the reaction completed, the catalyst was filtered and washed with water. The filtrates were collected, diluted with isopropanol and cooled to ±5° C. to precipitate the dipeptide which was then recovered by filtration, washed with isopropanol and MeCN at room temperature and then dried. The dipeptide was isolated with a yield of 85%.

Example 3

Synthesis of Boc-Gly-Gly-Val-Leu-OH (SEQ ID NO 19)

On one hand, H-Val-Leu-OH (1 eq.) was added to a solution of MSA (2.72 eq.) in AcOEt. The slurry was stirred at 25° C. until a solution was obtained. The solution was then cooled to −15° C. On the other hand, Boc-Gly-Gly-OH (1.05 eq., commercially available) was added together with NMM (1.0 eq.), AcOEt and DMF. The slurry was stirred until complete dissolution and then cooled to −25° C. IBCF (1.0 eq.) was added to the Boc-Gly-Gly-OH solution to activate the carboxylic function. The silylated Val-Leu was then added and left to stir at least 30 min. The reaction mixture was conditioned to 25° C. before being quenched by the addition of water. The mixture was then diluted with AcOEt and washed with a solution of $KHSO_4$ under stirring. The aqueous phase was discarded and the organic layer was washed again with a solution of NaCl. The organic phase was finally concentrated and the tetrapeptide crystallized under gentle stirring for at least 8 h at 5° C. The solid was recovered by filtration, once washed with cold AcOEt at 5° C. After drying under vacuum, 85% of Boc-Gly-Gly-Val-Leu-OH (SEQ ID NO 19) was recovered.

Example 4

Synthesis of Z-Glp-Pro-OH

Z-Glp-OH.DCHA (commercially available, 1 eq.) was diluted in AcOEt and neutralized by the addition of an aqueous solution of $KHSO_4$. The organic phase was collected and the aqueous phase was extracted with another volume of AcOEt. The combined organic phases were then washed with water and the solvent (AcOEt) was replaced with MeCN. Suc-OH (1.05 eq.) was dissolved in the solution of Z-Glp-OH which was then cooled to −5° C. DCC (1.1 eq.) dissolved in MeCN was added slowly to the solution keeping the reaction temperature below 5° C. The reaction was allowed to warm to 25° C. over at least 4 h. The excess of DCC was neutralized with AcOH (0.05 eq.) and the suspension was cooled to 10° C. before filtering the DCU precipitated which was then washed with MeCN. The resulting solution was warmed to 25° C. H-Pro-OH (2.0 eq.) was added to a solution of MeCN and (1.9 eq.) of MSA. The suspension was heated to 45° C. and left stirring until a clear solution was obtained. The solution was then cooled to 25° C. The silylated proline solution was added to the solution of Z-Glp-OSu and left to stir for at least 3 h at 25° C. The coupling solution was diluted with water and MeCN was evaporated in vacuo at a maximum temperature of 65° C. The remaining slurry was then diluted with water and the precipitate was left stirring for at least 10 h at 5° C. The solid was filtered, washed with water. After drying under vacuum 80% of Z-Glp-Pro-OH was recovered.

Example 5

Synthesis of Z-Glp-Pro-Gly-OH

Two solutions were prepared before the peptide coupling. Solution A: H-Gly-OH (1.2 eq.) was dissolved in MSA (3.0 eq.) at maximum 60° C. The suspension was cooled down to 25° C., diluted with DCM and stirred for at least 8 hours before being cooled to −15° C. In solution B, the carboxylic function of the Z-Glp-Pro-OH was dissolved with DCM and NMM (1.05 eq.). The solution was cooled to −15° C. The carboxylic acid was activated with IBCF (1.05 eq.) and the silylated solution A was then added to the slurry. The slurry was stirred for at least 0.5 h and left to warm to 25° C. The mixture was quenched with water and the addition of a solution of $KHSO_4$ under stirring precipitated the peptide. The solid was filtered and washed with water. After drying under vacuum, 80% of Z-Glp-Pro-Gly-OH was recovered.

Example 6

Synthesis of H-Gln-Pro-Gly-OH

Z-Glp-Pro-Gly-OH (1 eq.) was dissolved under stirring in DMA at 25° C. and $NH_4OH$ 25% (6 eq.) was added in such way that the temperature did not rise above 30° C. The mixture was stirred for at least 4 h at 25° C. The solution was concentrated under vacuum till the pH was ≤3. The concentrate was diluted with a NaCl aqueous solution and the pH was adjusted to 2.5 with a solution of $KHSO_4$. The resulting aqueous solution was washed twice with IPE and then extracted three times with n-BuOH at 25° C. The organic layers were combined and washed with water. The resulting organic solution was concentrated under reduced pressure. The concentrated solution was diluted with ethanol and water at 20° C. and Pd/C (0.02 eq.) was added to the peptide solution. The solution was stirred at 20° C. followed by the introduction of hydrogen under pressure (0.3 bar). The solution was stirred for at least 2 hours and the completion of the reaction was checked by HPLC. The solution was filtered to remove the catalyst and, after one washing with demineralised water, the pH of the solution was adjusted to 6.0<pH<6.5 with an aqueous solution of $NaHCO_3$. The free tripeptide was then precipitated by addition of ethanol. The solution was left to mature at 25° C. for 3 hours. The solid was filtered and washed with ethanol. After drying under vacuum, 60% of H-Gln-Pro-Gly-OH was recovered.

Example 7

Synthesis of H-Val-Gln-Pro-Gly-OH (SEQ ID NO 4)

H-Gln-Pro-Gly-OH (1 eq.) was added to $H_2O$ containing DIPEA (2.00 eq.). The slurry was stirred at 25° C. until a clear solution was observed and was then cooled to 0° C. Z-Val-OSu (1.1 eq.) was dissolved in MeCN at 25° C. until a clear solution was obtained and was then cooled to 0° C. The Z-Val-OSu solution was added to the solution of H-Gln-Pro-Gly-OH in such way that the temperature did not rise above 5° C. Then the mixture was stirred for at least 2 h. The peptide solution was concentrated and then diluted with a $KHSO_4$ solution and stirred for a few minutes. This aqueous solution was washed twice with a mixture of IPE and AcOEt. The organic phases were discarded and the aqueous phase was extracted 2 times with a 20% i-BuOH in DCM solution. The organic phases were collected and concentrated under reduced pressure until water content in the evaporates was ≤1% weight. The solution of the protected tetrapeptide was then precipitated in IPE at 25° C. Z-Val-Gln-Pro-Gly-OH (SEQ ID NO 16) was collected by filtration washed with IPE and dried under vacuum until IPE content in the peptide was <5% weight. The protected fragment was dissolved in methanol at 30° C. and Pd/C (0.02 eq.) was added to the peptide solution. The solution was stirred at 20° C. followed by the introduction of hydrogen under pressure (0.3 bar). After stirring for 3 hours the solution was filtered to remove the catalyst which was washed with methanol. After evaporation, the free tetrapeptide was then precipitated by transferring the solution into MeCN at 10° C. The solid was filtered and washed with MeCN. After drying under vacuum, 60% of H-Val-Gln-Pro-Gly-OH (SEQ ID NO 4) was recovered.

Example 8

Synthesis of AcOH.H-Gly-Gly-Val-Leu-Val-Gln-Pro-Gly-OH (SEQ ID NO 1)

H-Val-Gln-Pro-Gly-OH (SEQ ID NO 4) (1.0 eq.) was silylated by adding it to a solution of DMA containing MSA (3.2 eq.) at a temperature ≤40° C. until a clear solution was observed. This solution was then cooled to −15° C. Boc-Gly-Gly-Val-Leu-OH (1.05 eq. (SEQ ID NO 18)) was dissolved in DMA with Dipea (1.05 eq.) until a clear solution was obtained. The solution was cooled to −15° C. Pyridine (1.0 eq.) and PivCl (1.0 eq.) were added to the solution of Boc-Gly-Gly-Val-Leu-OH (SEQ ID NO 17) to activate the acid function. The solution of the silylated H-Val-Gln-Pro-Gly-OH (SEQ ID NO 4) was then transferred as quickly as possible to the solution of the activated tetrapeptide. The reaction medium was stirred for at least 0.5 h and left to warm to −5° C. The reaction mixture was neutralized at −5° C. by addition of 5% $KHSO_4$ and was then concentrated under reduced pressure. This solution was diluted successively with water and i-BuOH. The pH was adjusted to 2.5 by the controlled addition of a 5% aqueous $KHSO_4$ solution, and then DCM was introduced to extract the octapeptide. The aqueous solution was discarded and the organic phase was once washed with a solution of NaCl. The organic phase was then concentrated under reduced pressure and the solvent was replaced with glacial AcOH until water content was <2% weight and i-BuOH content <2% weight in the evaporates. In order to avoid possible problems such as for example gelification of the deprotection mixture, the protected octapeptide (SEQ ID NO 1) was isolated by precipitation by transferring the peptidic solution in a mixture of IPE and MeCN at 25° C. The Boc-Gly-Gly-Val-Leu-Val-Gln-Pro-Gly-OH (SEQ ID NO 20) was recovered by filtration, washed with IPE and dried until IPE content was <5% weight. To perform the deprotection step, the octapeptide was then dissolved in AcOH at room temperature.

To remove the Boc group, HCl 4M in dioxane (about 3.5 eq.) was added to the peptidic solution and the mixture was stirred at maximum 45° C. for at least 2 h. The final peptide was recovered by precipitation in a mixture of IPE and MeCN at 25° C. The solid was filtered, washed with IPE and with MeCN. After drying under vacuum at 40° C., 80% of HCl.H-Gly-Gly-Val-Leu-Val-Gln-Pro-Gly-OH (SEQ ID NO 1) was recovered. The peptide was solubilised in a 0.05M ammonium acetate buffer solution at 25° C., adjusted to 4.5<pH<5.0 with a 25% $NH_3$ solution, and then diluted with MeCN. This solution was filtered and purified as described in example 7.

Example 9

Purification of AcOH.H-Gly-Gly-Val-Leu-Val-Gln-Pro-Gly-OH (SEQ ID NO 1)

The chromatography was operated on an Amberchrom CG161 m, using as mobile phases: A="aqueous": 0.05 M $NH_4OAc$ (pH ~7.5) and B="organic": 0.05 $NH_4OAc$ in 50/50 HPW/MeCN. The stationary phase was first conditioned with a 10% solution of B, the crude product obtained in example 7 was then injected to the stationary phase and washed with a 10% solution of B. The eluent was then added (22% B) and the stationary phase was then washed with a 100% solution of B. The pooled pure fractions obtained by purification were collected and diluted 2 times with water (HPW). The same stationary phase was used as for the purification step and two new mobiles phases were prepared: A=1000/0/6 HPW/MeCN/AcOH (v/v) and B=700/300/6 HPW/MeCN/AcO H (v/v). The pooled fractions were loaded on the column, previously equilibrated with mobile phase A. The column was then washed again with 4 column volumes of mobile phase A and the peptide was then eluted with mobile phase B.

Example 10

Freeze-Drying of AcOH.H-Gly-Gly-Val-Leu-Val-Gln-Pro-Gly-OH (SEQ ID NO 1)

The solution of the peptide obtained in example 9 was concentrated under vacuum and lyophilized in GORE™ LYOGUARD® freeze-drying trays. The peptide solution was placed into a freeze-dryer (GT4 Edwards/Kniese) for lyophilisation. The freeze-drying trays were cooled to −40° C. for 3 h, then the temperature was raised to 20° C. under vacuum (0.22 mbar) for 17 h. After finishing main drying the temperature was maintained to 20° C. for 4 h with a vacuum adjusted to 0.02 mbar. A white powder of AcOH.H-Gly-Gly-Val-Leu-Val-Gln-Pro-Gly-OH (SEQ ID NO 1) was obtained.

Example 11

Precipitation of AcOH.H-Gly-Gly-Val-Leu-Val-Gln-Pro-Gly-OH (SEQ ID NO 1)

The solution of the peptide obtained in example 9 was concentrated under vacuum conditions and the precipitate was collected by filtration and dried under vacuum. A white powder of AcOH.H-Gly-Gly-Val-Leu-Val-Gln-Pro-Gly-OH (SEQ ID NO 1) was obtained.

Examples 12-13

Figure 5:
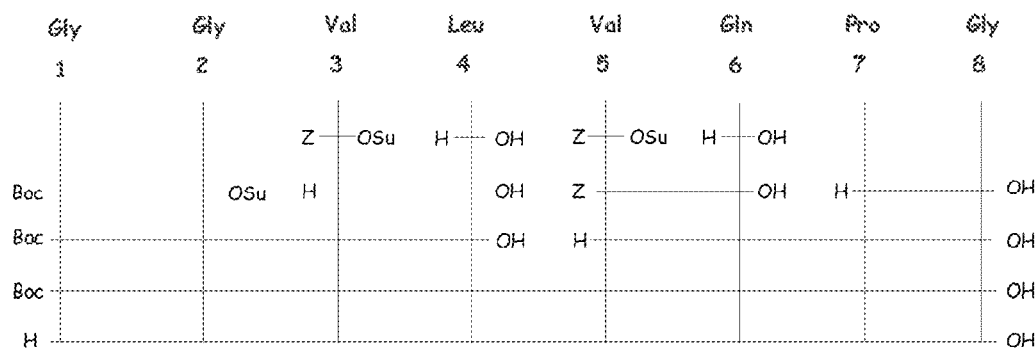
FIG. 5 illustrates scheme 5, which is an embodiment of scheme 3 for synthesizing the octapeptide of SEQ ID NO 1.

A second synthetic approach is described in scheme 3 (FIG. 3) and a particular embodiment thereof is given in the following scheme 5 (FIG. 5). This approach is illustrated by the examples hereafter.

Example 12

Synthesis of Z-Val-Gln-OH

H-Gln-OH (2 eq.) and NaHCO$_3$ (2 eq.) were dissolved under stirring in water at maximum 45° C. and then cooled to about 5° C. Z-Val-OSu (1 eq.) was dissolved in MeCN and added in the aqueous solution in such way that the temperature did not rise above 10° C. The mixture was stirred for at least 1 h at ±5° C. before being warmed to room temperature for at least two hours. The peptide solution was concentrated under vacuum, diluted with water and washed twice with AcOEt. The aqueous phase was then diluted with i-BuOH and the pH was adjusted to 2.5 with a solution of KHSO$_4$. DCM was then added to extract the peptide into the organic phase which was washed with a 5% weight NaCl solution and finally with water. The organic phase was collected and concentrated under reduced pressure until water content in the evaporates was <1% weight. The concentrate was diluted with hot isopropyl acetate and left to cool to 25° C. under gentle stirring to crystallize the peptide. The solid was recovered by filtration, once washed with AcOiPr at 25° C. and dried under vacuum until AcOiPr content in the peptide was ≤5% weight. After drying under vacuum not less than 70% of Z-Val-Gln-OH was recovered.

Example 13

Synthesis of H-Val-Gln-Pro-Gly-OH (SEQ ID NO 4)

H-Pro-Gly-OH (1.15 eq.) was mixed in water with Dipea (1.05 eq.) until complete dissolution, then DMA was added. The solution was cooled to −10° C. Z-Val-Gln-OH was dissolved in DMA and the resulting solution was cooled to −15° C. Dipea (1.05 eq.) was introduced to neutralize the carboxylic function, and then pyridine (1.05 eq.) and PivCl were introduced to activate the acid function. The Pro-Gly solution was transferred to the activated dipeptide as quickly as possible and the slurry was stirred for at least 0.5 hours and left to warm to room temperature. The reaction mixture was neutralized by addition of water, diluted with a 5% aqueous solution of NaHCO$_3$ and washed 3 times with AcOEt. The pH was then adjusted to 2.5 with 5% KHSO$_4$ and the peptide is extracted three times with a 20% i-BuOH in DCM solution. The organic phases were collected and concentrated under reduced pressure until water content in the evaporates was ≤1% weight. The solution of the protected tetrapeptide was then precipitated in IPE at 25° C. Z-Val-Gln-Pro-Gly-OH (SEQ ID NO 16) was collected by filtration, washed with IPE and dried under vacuum until IPE content in the peptide was <5% weight. The protected fragment is recrystallized in a mixture of iPrOH and AcOEt before proceeding to the deprotection step. Z-Val-Gln-Pro-Gly-OH (SEQ ID NO 16) was dissolved in methanol at 30° C. and Pd/C (0.02 eq.) was added to the peptide solution. The solution was stirred at 30° C. followed by the introduction of hydrogen under pressure (0.3 bar). The solution was stirred for at least 3 hrs and the completion of the reaction was checked by HPLC. The solution was filtered to remove the catalyst and washed with methanol. After evaporation, the free tetrapeptide was then precipitated by transferring the solution in MeCN at 10° C. The solution was left to mature at 10° C. for at least 30 minutes. The solid was filtered and washed with MeCN. After drying under vacuum not less than 60% of H-Val-Gln-Pro-Gly-OH (SEQ ID NO 4) was recovered. This product can be coupled as described in example 8 above to provide H-Gly-Gly-Val-Leu-Val-Gln-Pro-Gly-OH (SEQ ID NO 1).

Examples 14-19

Figure 6:
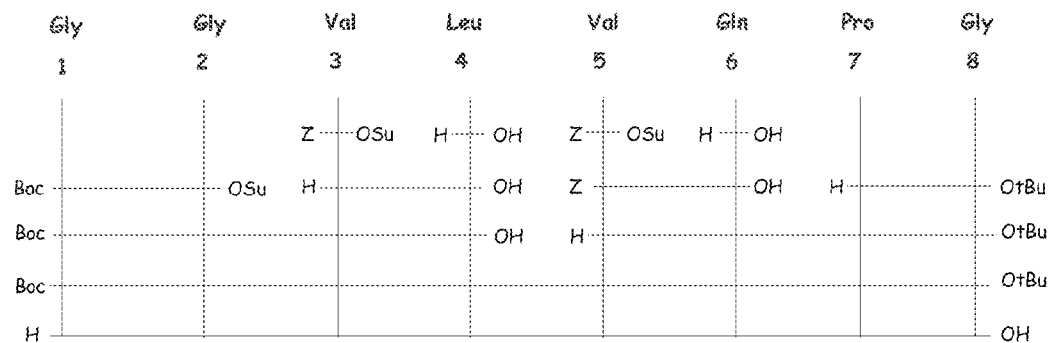
FIG. 6 illustrates scheme 6, which is an embodiment of scheme 3 for synthesizing the octapeptide of SEQ ID NO 1.

A third synthetic approach is described in scheme 3 (FIG. 3) and another particular embodiment thereof is given in the following scheme 6 (FIG. 6). This approach is illustrated by the examples hereafter.

Example 14

Synthesis of Boc-Gly-Gly-OSu

Boc-Gly-Gly-OH and Suc-OH (1.1 eq.) were dissolved in iPrOH and DIC (Diisopropylcarbodiimide) (1.1 eq.) was added slowly to the solution at about 25° C. The reaction was stirred at 25° C. for at least 4 h before cooling the suspension to 5° C. The activated dipeptide was recovered by filtration at 5° C. and washed with cold iPrOH. The Boc-Gly-Gly-OSu was isolated after drying with a yield of 85%.

Example 15

Synthesis of Boc-Gly-Gly-Val-Leu-OH (SEQ ID NO 17) via Boc-Gly-Gly-OSu

On one hand, H-Val-Leu-OH (1.05 eq.) was added to a solution of MSA (2.7 eq.) in AcOEt. The slurry was stirred at 25° C. until a solution was obtained. On the other hand, Boc-Gly-Gly-OSu (1 eq.) was partially dissolved in a mixture of AcOEt and DMA. The dipeptide solution was then transferred to the Boc-Gly-Gly-OSu solution under stirring at 25° C. When the coupling was completed (checked by HPLC), unreacted OSu ester was neutralized with DMAPA (0.05 eq.). The reaction was then quenched by addition of water, diluted with AcOEt and washed with a solution of KHSO$_4$ under stirring. The aqueous phase was discarded and the organic layer was washed again with a solution of NaCl and finally with water. The organic phase was finally concentrated under vacuum until the water content in the evaporates was <1% weight and the solution was diluted with hot isopropyl ether and left to cool to 25° C. under gentle stirring to crystallize the peptide. The solid was recovered by filtration, once washed with IPE at 25° C. After drying under vacuum, 80% of Boc-Gly-Gly-Val-Leu-OH (SEQ ID NO 17) was recovered.

Example 16

The same procedure as in example 15 was followed but using MTBE instead of IPE for dilution and washing. The same yield of Boc-Gly-Gly-Val-Leu-OH (SEQ ID NO 17) was recovered while MTBE is cheaper and safer than IPE.

Example 17

Synthesis of H-Val-Gln-Pro-Gly-OtBu (SEQ ID NO 18)

Z-Pro-Gly-OtBu was dissolved in AcOEt at 25° C. and Pd/C (0.02 eq.) was added to the peptide solution. The solution was stirred at 25° C. followed by the introduction of hydrogen under pressure (0.3 bar). After the reaction was considered as complete by HPLC, the solution was filtered to remove the catalyst which was washed with AcOEt. The solution of H-Pro-Gly-OtBu (1.05 eq.) was cooled to −15° C. Z-Val-Gln-OH was dissolved in a mixture of DMA and AcOEt and the resulting solution was cooled to −15° C. Dipea (1.05 eq.) was introduced to neutralize the carboxylic function, and then pyridine (1.05 eq.) and PivCl were introduced to activate the acid function. The H-Pro-Gly-OtBu solution was transferred to the activated dipeptide as quickly as possible and the slurry was stirred for at least 0.5 hours and left to warm to room temperature. The reaction mixture was neutralized by addition of water, diluted with AcOEt and the organic phase was washed with a 5% aqueous solution of $KHSO_4$, with a 5% aqueous solution of $NaHCO_3$, with a 5% aqueous solution of NaCl and finally with water. The organic phase was collected and concentrated under reduced pressure until water content in the evaporates was ≤1% weight. The concentrate was diluted with hot isopropyl ether and left to cool to 25° C. under gentle stirring to crystallize the peptide. The solid was recovered by filtration, once washed with hot IPE and dried under vacuum until IPE content in the peptide was <5% weight. Z-Val-Gln-Pro-Gly-OtBu (SEQ ID NO 22) was dissolved in ethanol at room temperature and Pd/C (0.02 eq.) was added to the peptide solution. The solution was stirred at 25° C. followed by the introduction of hydrogen under pressure (0.3 bar). The solution was stirred for at least 2 hrs and the completion of the reaction was checked by HPLC. The solution was filtered to remove the catalyst and washed with ethanol. After evaporation, the free tetrapeptide was then precipitated by transferring the solution in MTBE at −10° C. The solution was left to mature at −10° C. for at least 30 minutes. The solid was filtered and washed with MTBE. After drying under vacuum not less than 80% of H-Val-Gln-Pro-Gly-OtBu (SEQ ID NO 18) was recovered.

Example 18

Synthesis of HCl.H-Gly-Gly-Val-Leu-Val-Gln-Pro-Gly-OH (SEQ ID NO 1)

Z-Val-Gln-Pro-Gly-OtBu (SEQ ID NO 21) was dissolved in DMA at 25° C. and Pd/C (0.02 eq.) was added to the peptide solution. The solution was stirred at 25° C. followed by the introduction of hydrogen under pressure (0.3 bar). After the reaction was considered as complete by HPLC, the solution was filtered to remove the catalyst which was washed with DMA. Boc-Gly-Gly-Val-Leu-OH (1.05 eq.) (SEQ ID NO 17) was dissolved in DMA and the resulting solution was cooled to −15° C. Dipea (1.05 eq.) was introduced to neutralize the carboxylic function, and then pyridine (1 eq.) and PivCl were introduced to activate the acid function. The solution of H-Val-Gln-Pro-Gly-OtBu (SEQ ID NO 2) (1.0 eq.) in DMA cooled to −15° C. was transferred to the activated tetrapeptide as quickly as possible and the slurry was stirred for at least 0.5 hours and left to warm to about −5° C. The reaction mixture was quenched with water and then diluted by addition of hot water to precipitate the peptide. The slurry was left to stir at room temperature and the solid was filtered, washed with an aqueous solution of $KHSO_4$, with an aqueous solution of $NaHCO_3$ and finally with water. The solid was dried under reduced pressure until water content was ≤3% weight. To remove the Boc group, the protected octapeptide (SEQ ID NO 1) was dissolved in AcOH and HCl 1M in AcOH (7 eq.) was added. The mixture was stirred at about 30° C. for about 5 hrs. The final peptide was recovered by precipitation in a mixture of MeCN and IPE at 25° C. The solid was filtered, washed several times with IPE and finally with MeCN. After drying under vacuum at 40° C., 80% of HCl.H-Gly-Gly-Val-Leu-Val-Gln-Pro-Gly-OH (SEQ ID NO 1) was recovered.

Example 19

Synthesis of H-Gly-Gly-Val-Leu-Val-Gln-Pro-Gly-OH (SEQ ID NO 1)

Boc-Gly-Gly-Val-Leu-OH (1.0 eq.) (SEQ ID NO 17), H-Val-Gln-Pro-Gly-OtBu (SEQ ID NO 18) (1.0 eq.) and Hobt (1.1 eq.) were dissolved in DMA at room temperature until a clear solution was obtained. The solution was cooled to about −5° C. and EDC (1.1 eq.) was added to the solution to initiate the coupling. The mixture was stirred at −5° C. until completion of the coupling (progress of reaction was followed by HPLC). The reaction mixture was diluted by addition of water what made the peptide precipitate. The solid was filtered, washed with an aqueous solution of $KHSO_4$, with an aqueous solution of $NaHCO_3$ and finally with water. The solid was dried under reduced pressure. To remove the Boc group, the protected octapeptide was dissolved in AcOH and HCl 4M in dioxane (12 eq.) was added. The mixture was stirred at 25° C. for about 2 h. The final peptide was recovered by precipitation in IPE at 25° C. The solid was filtered, washed several times with IPE and finally with MeCN. After drying under vacuum at 40° C., 80% of HCl.H-Gly-Gly-Val-Leu-Val-Gln-Pro-Gly-OH (SEQ ID NO 1) was recovered. The peptide was solubilised in a 0.05M ammonium acetate buffer solution at 25° C., adjusted to 4.5≤pH<5.0 with a 25% $NH_3$ solution, and then diluted with MeCN. This solution was filtered and purified as described in example 9.

Example 20

Synthesis of HCl.H-Gly-Gly-Val-Leu-Val-Gln-Pro-Gly-OH (SEQ ID NO 1)

Z-Val-Gln-Pro-Gly-OtBu (SEQ ID NO 21) was dissolved in DMA at 25° C. and Pd/C (0.02 eq.) was added to the peptide solution. The solution was stirred at 25° C. followed by the introduction of hydrogen under pressure (0.3 bar). After the reaction was considered as complete by HPLC, the solution was filtered to remove the catalyst which was washed with DMA. Boc-Gly-Gly-Val-Leu-OH (1.05 eq.) (SEQ ID NO 17) was dissolved in DMA and the resulting solution was cooled to −15° C. Dipea (1.05 eq.) was introduced to neutralize the carboxylic function, and then pyridine (1 eq.) and PivCl were introduced to activate the acid function. The solution of H-Val-Gln-Pro-Gly-OtBu (SEQ ID NO 18) (1.0 eq.) in DMA cooled to −15° C. was transferred to the activated tetrapeptide as quickly as possible and the slurry was stirred for at least 0.5 hours and left to warm to about −5° C. The reaction mixture was quenched with water and then diluted by addition of hot deionized water to precipitate the peptide. The slurry was left to stir at room temperature and the solid was filtered, washed with an aqueous solution of $KHSO_4$, with an aqueous solution of $NaHCO_3$ and finally with water. The solid was dried under reduced pressure until water content was <3% weight. To remove the Boc group, the protected octapeptide was dissolved in AcOH and HCl 1 M in AcOH (7 eq.) was added. The mixture was stirred at about 30° C. for about 5 hrs (until completion of the reaction followed by HPLC). The final peptide was recovered by crystallization by the addition of MeCN to the deprotection mixture followed by the addition of IPE. The solid was filtered, washed several times with IPE and finally with MeCN. After drying under vacuum at 40° C., 80% of HCl.H-Gly-Gly-Val-Leu-Val-Gln-Pro-Gly-OH (SEQ ID NO 1) was recovered.

Example 21

Crystallization of AcOH.H-Gly-Gly-Val-Leu-Val-Gln-Pro-Gly-OH (SEQ ID NO 1)

Figure 11:
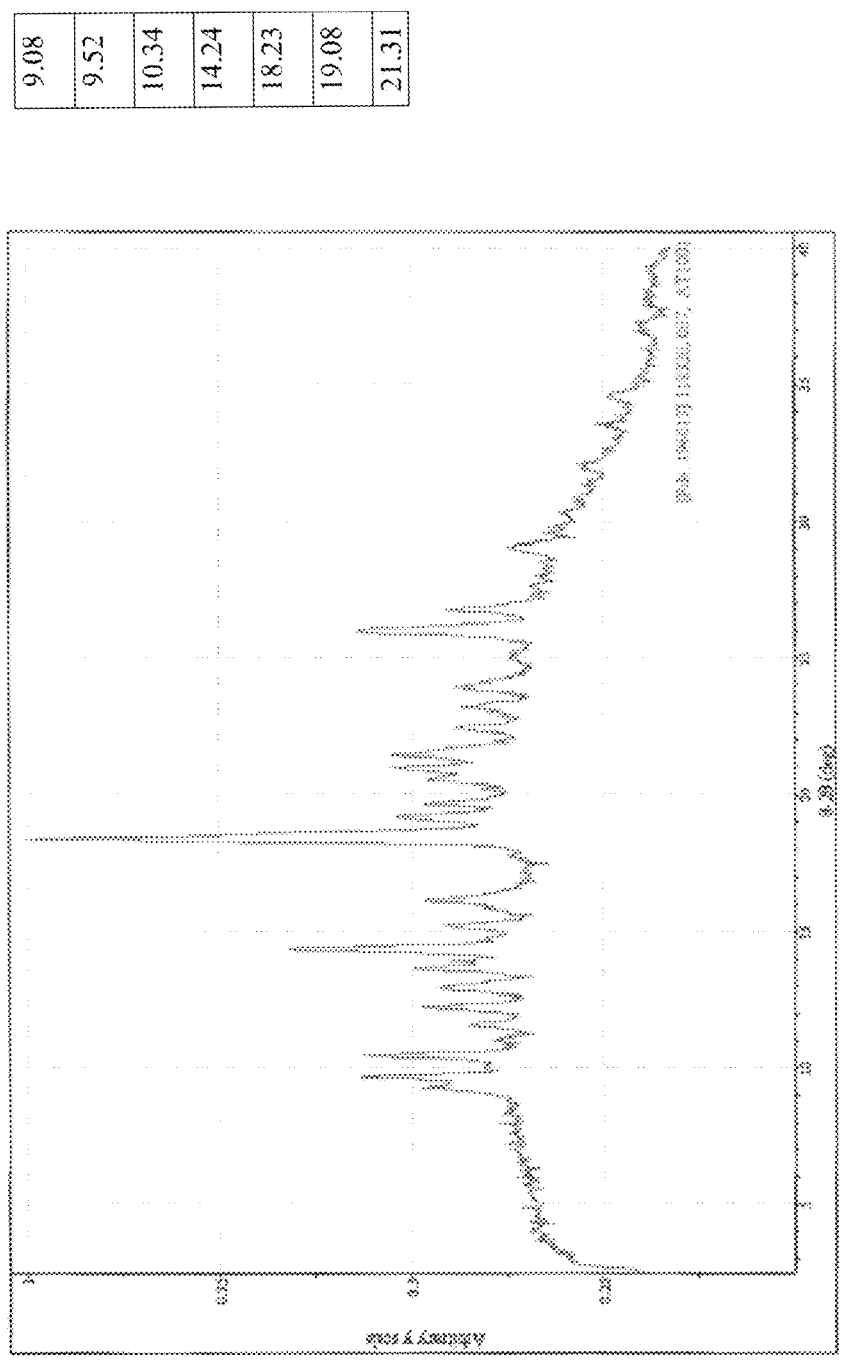
FIG. 11 shows an exemplary X-ray powder diffraction (XRPD) for Larazotide acetate.

The HCl.H-Gly-Gly-Val-Leu-Val-Gln-Pro-Gly-OH (SEQ ID NO 1) was dissolved in water and ammonium acetate (±1.25 eq.) was added to the aqueous solution at 25° C., the pH was then adjusted to ±4.5 with an aqueous $NH_3$ solution in order to crystallize the peptide. After several hours of stirring at 25° C., the solid was then filtered and dried under vacuum until the water content was ≤5.0% weight. After drying under vacuum not less than 80% of AcOH.H-Gly-Gly-Val-Leu-Val-Gln-Pro-Gly-OH (SEQ ID NO 1) was recovered. The crystallinity of the recovered material was confirmed by XRPD. An exemplary XRPD pattern of crystalline larazotide acetate is shown in FIG. 11 and is described in more depth below.

Example 22

Comparative Studies of Crystalline and Amorphous Peptide Materials

The objective of this example was to isolate amorphous larazotide acetate (an acetate salt of the peptide of SEQ ID NO 1), and to conduct comparative studies of amorphous larazotide acetate versus crystalline larazotide acetate, identified as Lot 020.

Two experiments were conducted using varying solubilization conditions, with the objective of isolating amorphous larazotide acetate. For each experiment, 1 g of crystalline larazotide acetate (Lot 020) is dissolved in 1% acetic acid solution at a concentrations of 1 g/L (identified as lot E120040-1 g/l) "amorphous lot 1 g/l" and 4 g/L (identified as lot E120040-4-g/l) "amorphous lot 4 g/l", respectively. The resulting solutions were transferred into round bottom flasks and frozen using an acetone/dry ice bath and then lyophilized using a laboratory lyophilizer (no pressure control). Upon isolation, the materials were tested by X-ray diffraction in order to assess whether the isolated material was amorphous or shows crystalline characteristics.

In addition, the isolated materials were tested using the common release tests of: HPLC (assay purity, impurities), water content, acetate content, and peptide content.

Figure 7:
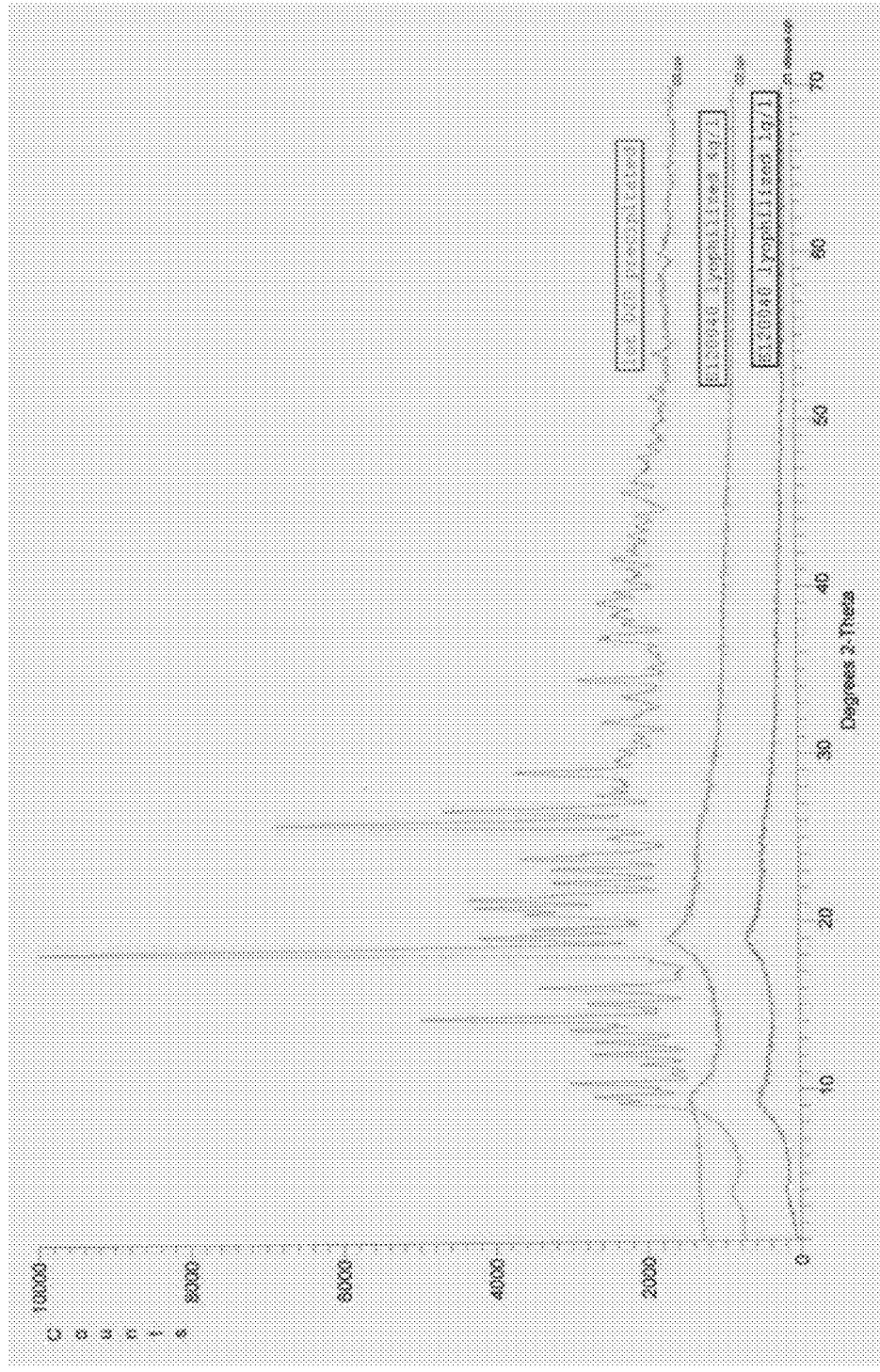
FIG. 7 shows exemplary XRPD profiles of various solid state forms of Larazotide acetate.

Upon isolation of the two lyophilized batches of larazotide acetate, XRPD was collected and compared to the crystalline larazotide acetate, which was used as the starting material for the experiments. As seen in FIG. 7, the isolated materials had XRPD profiles consisting of broad halos, which is characteristic of amorphous material. In contrast, the starting material, crystalline larazotide acetate (lot 020), exhibits a XRPD trace with a series of well-defined reflections which is consistent with a crystalline (or highly organized) material. XRPD conditions were as described in Example 24.

In addition, both the amorphous larazotide acetate batches as well as the crystalline larazotide acetate were tested for various quality attributes. This data is provided in Table 3. The appearance of the drug substance is examined visually. The evaluation includes observing if there is a lack of homogeneity and the color of the solid powder. HPLC was at a detection wavelength of 220 nm. Water content was determined using a Karl-Fisher titration. Acetate content was determined by ionic chromatography.

All three samples were white solids; water content was slightly higher in both amorphous lots. Acetate levels were also consistent over all samples tested. Peptide content was slightly lower in the amorphous lots (consistent with the slight increase in water content). Purity of the two amorphous lots was also lower and is attributed to the slight increases in the presence of the 12-mer impurity (comprising larazotide acetate with an extra residue 5-8 sequence peptide designated larazotide+[5-8] in Table 3) and the larazotide dimer impurity (designated dimer in Table 3).

TABLE 3

Chemical Analysis Characteristics of Larazotide Acetate

| Test | E120040-1 g/l | E120040-4 g/l | Lot 020 | Lot 020@[**] |
|---|---|---|---|---|
| Appearance | White solid | White solid | White solid | White solid |
| Water (w/w) | 2.5 | 1.5 | 0.5 | 0.6 |
| Acetate (w/w) | 5.5 | 6.7 | 5.4 | 5.6 |
| Peptide content (HPLC) | 92.4 | 92.6 | 94.9 | 93.4 |
| Purity (HPLC) | 99.1 | 99.0 | 99.7 | 99.7 |
| Identified Impurities: | | | | |
| GGVLV-amide | <0.05 | <0.05 | <0.05 | <0.05 |
| Des-amide | 0.25 | 0.25 | 0.21 | 0.17 |
| —OMe | <0.05 | <0.05 | <0.05 | <0.05 |
| acetylated | 0.08 | 0.11 | <0.02 | 0.02 |
| Larazotide + [5-8] | 0.15 | 0.20 | 0.02 | 0.03 |
| dimer | 0.11 | 0.12 | <0.05 | <0.05 |
| Largest Unknown Impurity | 0.05 (RRT1.16) | <0.05 | <0.05 | <0.05 |

[**]Lot 020@ is a retest of Lot 020

0.5 g of each of the three lots of larazotide acetate were used for determination of critical micellar concentration (CMC), which is an assessment of thermodynamic solubility using equilibrium surface tension measurements over 40 concentrations. These CMC data were determined in duplicate surface tension experiments by dilution of initially prepared stock solutions. Duplicate determinations were measured and reported in Table 4. Notably, the CMC value of the crystalline larazotide acetate is much lower than either lot of amorphous larazotide acetate, which is consistent with the apparent lower solubility of the crystalline material. The CMC solubility of both amorphous materials are equivalent. Overall, both the crystalline and amorphous larazotide acetate have a relatively low water solubility, which is consistent with the hydrophobic composition of the peptide.

TABLE 4

CMC Values for Larazotide Acetate

| Larazotide Acetate | CMC #1 (mg/ml) | CMC #2 (mg/ml) |
|---|---|---|
| Lot 020 | 1.92 | 1.93 |
| Lot E120040-1 g/L | 8.59 | 8.58 |
| Lot E120040-4 g/L | 8.72 | 8.74 |

The stock solutions were prepared (and the CMC values are reported above) based on an anhydrous free base equivalent. Thus, when preparing a 5 mg/ml stock solution of the crystalline sample, 5.342 mg powder was dissolved per ml of water (5/0.936). Likewise the 25 mg/ml sample of the amorphous lot 1 g/L was prepared by dissolving 27.06 mg/ml (25/0.924) and the 25 mg/ml of the amorphous lot 4 g/L was prepared by dissolving 27.00 mg/ml (27/0.926).

The crystalline larazotide acetate and amorphous lot 1 g/L were also tested for moisture uptake and loss over a range of relative humidity at 22° C. The moisture sorption isotherm was performed in 5% RH increments at 22° C. following an initial drying step (equilibration at near 0% RH and the same temperature for a period of 2 hours). The experiment was performed using an IGAsorp Moisture Sorption Analyzer from Hiden Analytical.

Each sample was loaded and allowed to equilibrate for 2 hours at near 0% RH at 22° C. prior to starting the isotherm. Following equilibration to the dry state, the relative humidity in the sample chamber was first increased in 5% RH steps to 95% RH, and then decreased in 5% RH steps back to near 0% RH. A 95% of equilibrium minimum was used for RTP analysis at each RH setting.

The resultant equilibrium sample mass at each RH setting was taken. The equilibrium moisture content as a percentage of dry mass was also reported for each RH step. This is calculated based on the relation between the equilibrium sample mass at that RH step and the sample mass determined at 0% RH (dry conditions).

Figure 8:
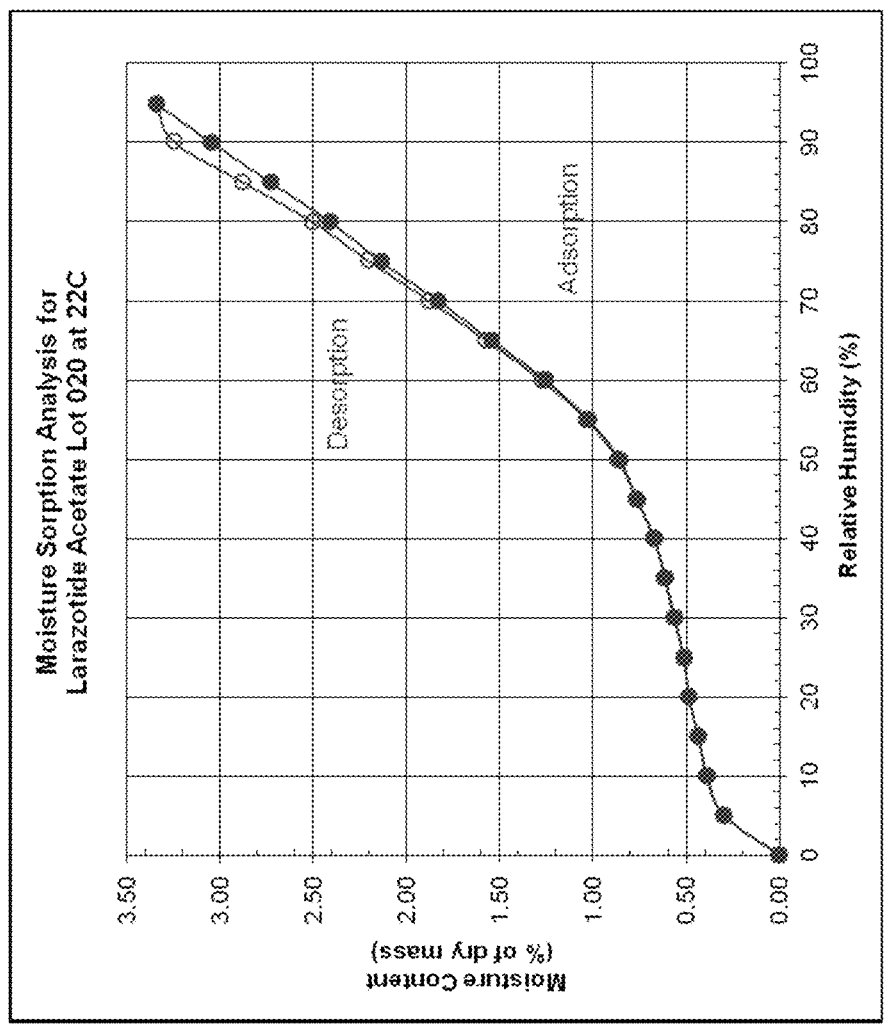
FIG. 8 shows an exemplary moisture sorption analysis for crystalline Larazotide acetate.
Figure 9:
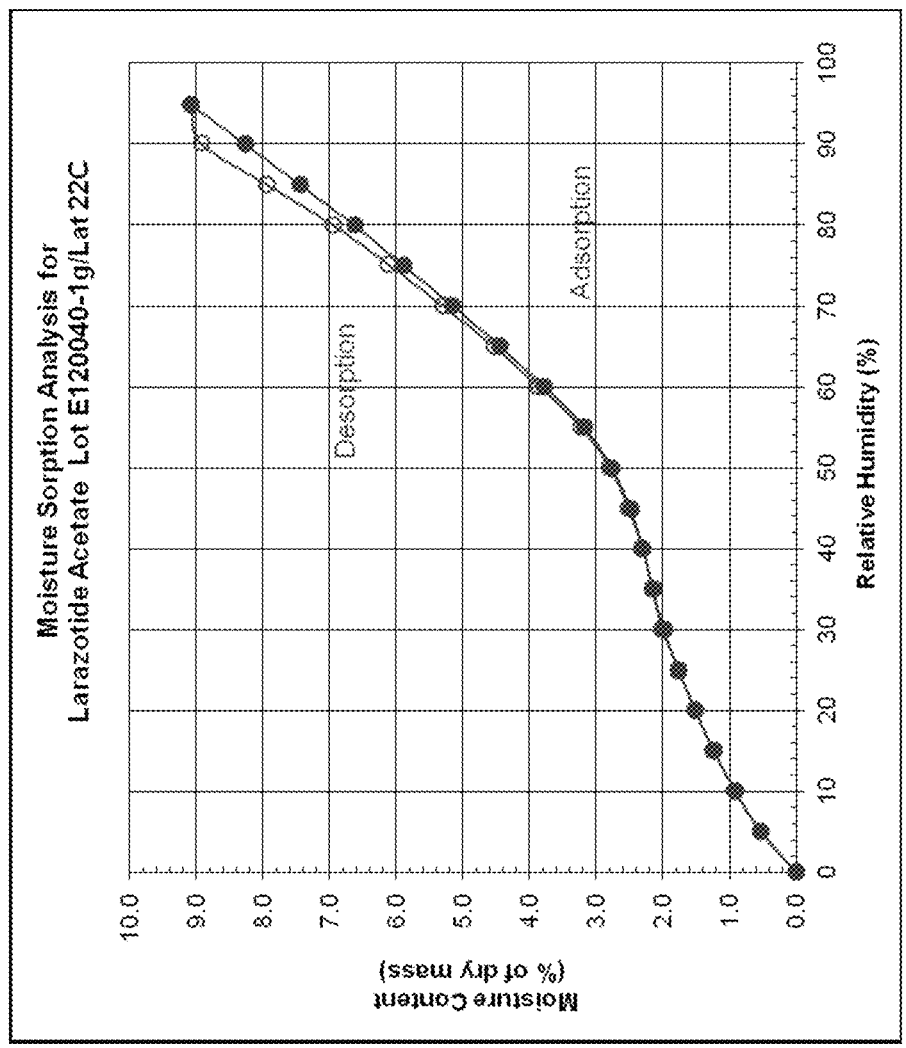
FIG. 9 shows an exemplary moisture sorption analysis for amorphous Larazotide acetate.

The data in FIG. 8 show that moisture uptake for the crystalline larazotide acetate sample is fairly exponential with some hysteresis at high RH levels and reaches a maximum uptake of 3.340% on a dry mass basis at 95% RH. For the amorphous lot 1 g/l sample, shown in FIG. 9, the moisture uptake is also exponential with some hysteresis at high RH levels and reaches a maximum uptake of 9.080% on a dry mass basis at 95% RH.

Hysteresis at high RH level is due to capillary action within and/or between powder particles. Capillary action works to draw moisture in during absorption but resists moisture loss during desorption, thus a lower RH (bigger driving force for drying) must be used to obtain the same level of equilibrium moisture content on the desorption side of the isotherm versus on the adsorption side of the isotherm. At all RH conditions, the crystalline larazotide acetate sample absorbs significantly less moisture than the amorphous lot 1 g/l sample.

An appropriate amount of amorphous larazotide acetate and crystalline larazotide acetate was used for a stability study to evaluate quality parameters (purity, impurities, assay and ID) for these materials under various storage conditions. Data was collected at two time points, namely at 1 month and at 2 months of storage under the conditions tested.

The stability data generated for amorphous and crystalline of larazotide acetate demonstrated that the crystalline material is quite stable. Long term stability data for the crystalline material shows no evidence of degradation at −20, 2-8 C and 25 C/60% RH. Only minimal degradation of the crystalline material is observed when stored at stressed conditions of 40 C/75% RH. In contrast, the amorphous form of larazotide acetate is notably less stable. Data was generated for storage of the three larazotide acetate samples stored at 40 C/75% RH. All three samples were analyzed at 1 and 2 months. The one and two month data is presented in FIG. 10.

Stability data for the two months of analysis show a minor decrease in overall purity of the crystalline larazotide acetate. In sharp contrast, both lots of amorphous larazotide acetate degraded at an overall rate of almost 10% per month in this storage condition. Data in Table 3 shows increases in the known degradation products for larazotide acetate. In addition, the raw data also shows a time dependent, measurable increase in other unknown impurities at RRT 0.98, 1.49, 1.51, 1.63, 1.64, 1.69, and 2.12. This study confirms the improved stability properties for crystalline Larazotide acetate over amorphous larazotide acetate. Taken as a whole the comparative data reveals that amorphous larazotide acetate has different physical properties than crystalline larazotide acetate, which may make amorphous larazotide acetate less suitable for pharmaceutical applications.

Example 23

Stability and Solubility of Larazotide Salts

Solubilities of Larazotide acetate and the corresponding chloride salt in water were tested at 20° C. after 14 hours of vigorous stirring in the presence of residual solid. Concentrations of peptide are measured by standardized HPLC. The chloride salt is more soluble than the acetate salt.

TABLE 5

Solubility of acetate and chloride salts

| Sample | Water Solubility at 20° C., in g/liter |
|---|---|
| Larazotide Acetate | 7.9 |
| Larazotide Chloride | ≥300 |

The stability of the chloride salt was tested at 25° C. without humidity control (in closed bottles). The stability of the acetate salt was determined at 25° C./60% RH. As shown below, the chloride salt is less stable than the acetate salt due to deamidation. The rate of deamidation of the chloride salt was about 1%/month. The rate of deamidation was about 0.05%/month for the acetate salt.

TABLE 6

Stability of Acetate and Chloride Salts

| Timepoint | % HPLC Area (purity) | Deamidated "Glu" % HPLC area |
|---|---|---|
| Larazotide Acetate | | |
| 0 | 98.7 | 0.19 |
| 1 | 98.4 | 0.22 |
| 2 | 98.2 | 0.26 |
| 3 | 97.7 | 0.40 |
| 6 | 96.1 | 0.60 |
| Larazotide Chloride | | |
| 0 | 98.4 | 1.06 |
| 1 | 97.8 | 1.85 |
| 2 | 96.1 | 3.02 |

Example 24

Characterization of Crystalline Larazotide Acetate

Eight lots of Larazotide acetate were characterized as crystalline by XRPD. XRPD analyses were performed using a Shimadzu XRD-6000 X-ray powder diffractometer using Cu Kα radiation. The instrument was equipped with a long fine focus X-ray tube. The tube voltage and amperage were set to 40 kV and 40 mA, respectively. The divergence and scattering slits were set at 1° and the receiving slit was set at 0.15 mm. Diffracted radiation was detected by a NaI scintillation detector. A θ-2θ continuous scan at 3°/min (0.4 sec/0.02° step) from 2.5 to 40° 2θ was used. A silicon standard was analyzed to check the instrument alignment. Data were collected and analyzed using XRD-61 00/7000 v. 5.0. Samples were prepared for analysis by placing them in a silicon sample holder. The remainder of the XRPD analyses were performed using an Inel XRG-3000 diffractometer equipped with a CPS (Curved Position Sensitive) detector with a 2θ range of 120°. Real time data were collected using Cu-Kα radiation at a resolution of 0.03° 2θ. The tube voltage and amperage were set to 40 kV and 30 mA, respectively. The monochromator slit was set at 5 mm by 160 μm. The pattern is displayed from 2.5-40° 2θ. Samples were prepared for analysis by packing them into thin-walled glass capillaries. Each capillary was mounted onto a goniometer head that is motorized to permit spinning of the capillary during data acquisition. The samples were analyzed for 5 min. Instrument calibration was performed using a silicon reference standard.

Comparison of the patterns indicated the same peak positions in each, suggesting that all eight samples are composed of the same solid form. This form has been designated Form A, and a representative XRPD pattern is shown in FIG. 11.

In addition to XRPD analysis, Form A was characterized by thermal methods and by automated moisture sorption/desorption. DSC was performed using a TA Instruments differential scanning calorimeter Q1000. The sample was placed into an aluminum DSC pan, and the weight accurately recorded. The pan was covered with a lid and then crimped. The sample cell was equilibrated at 0° C. and heated under a nitrogen purge at a rate of 10° C./min, up to a final temperature of 300° C. Indium metal was used as the calibration standard.

Figure 12:
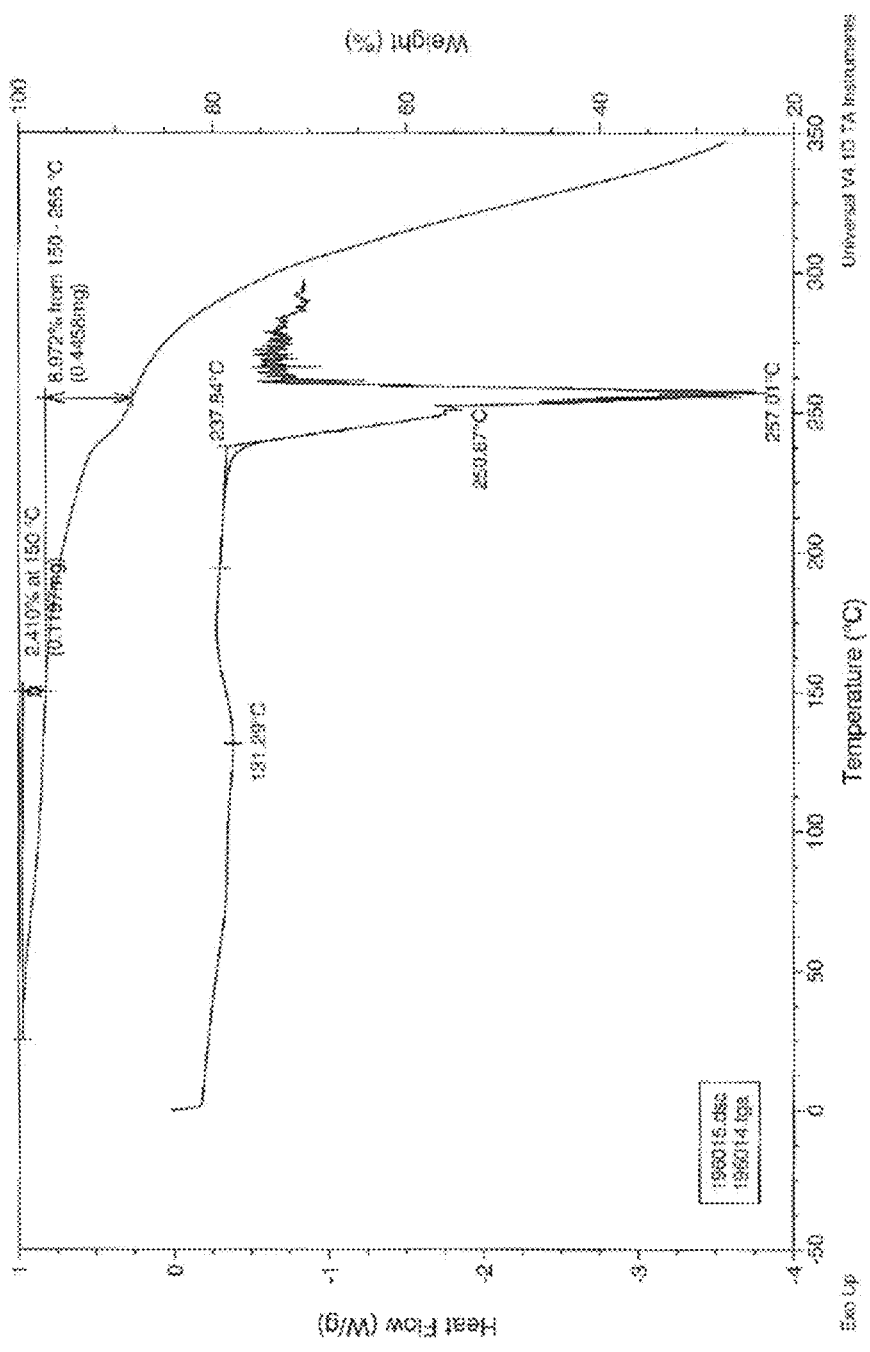
FIG. 12 shows an exemplary differential scanning calorimetry (DSC) and thermogravimetry (TG) of crystalline larazotide acetate.

The DSC transitions corresponded to TG weight losses (FIG. 12). A TG weight loss of 2.4% was observed from ambient temperature to 150° C., followed by an additional weight loss of 9% up to 255° C. A broad, low intensity endothermic transition with a peak maximum of 131° C. was observed by DSC and is consistent with a desolvation event. The DSC data indicated a second, noisy endothermic transition with an onset at 238° C. indicative of decomposition.

Moisture sorption/desorption data were collected on a VTI SGA-100 Vapor Sorption Analyzer. Sorption and desorption data were collected over a range of 5% to 95% relative humidity (RH) at 10% RH intervals under a nitrogen purge. Samples were not dried prior to analysis. Equilibrium criteria used for analysis were less than 0.0100% weight change in five minutes, with a maximum equilibration time of three hours if the weight criterion was not met. Data were not corrected for the initial moisture content of the samples. NaCl and PVP were used as calibration standards.

Figure 13:
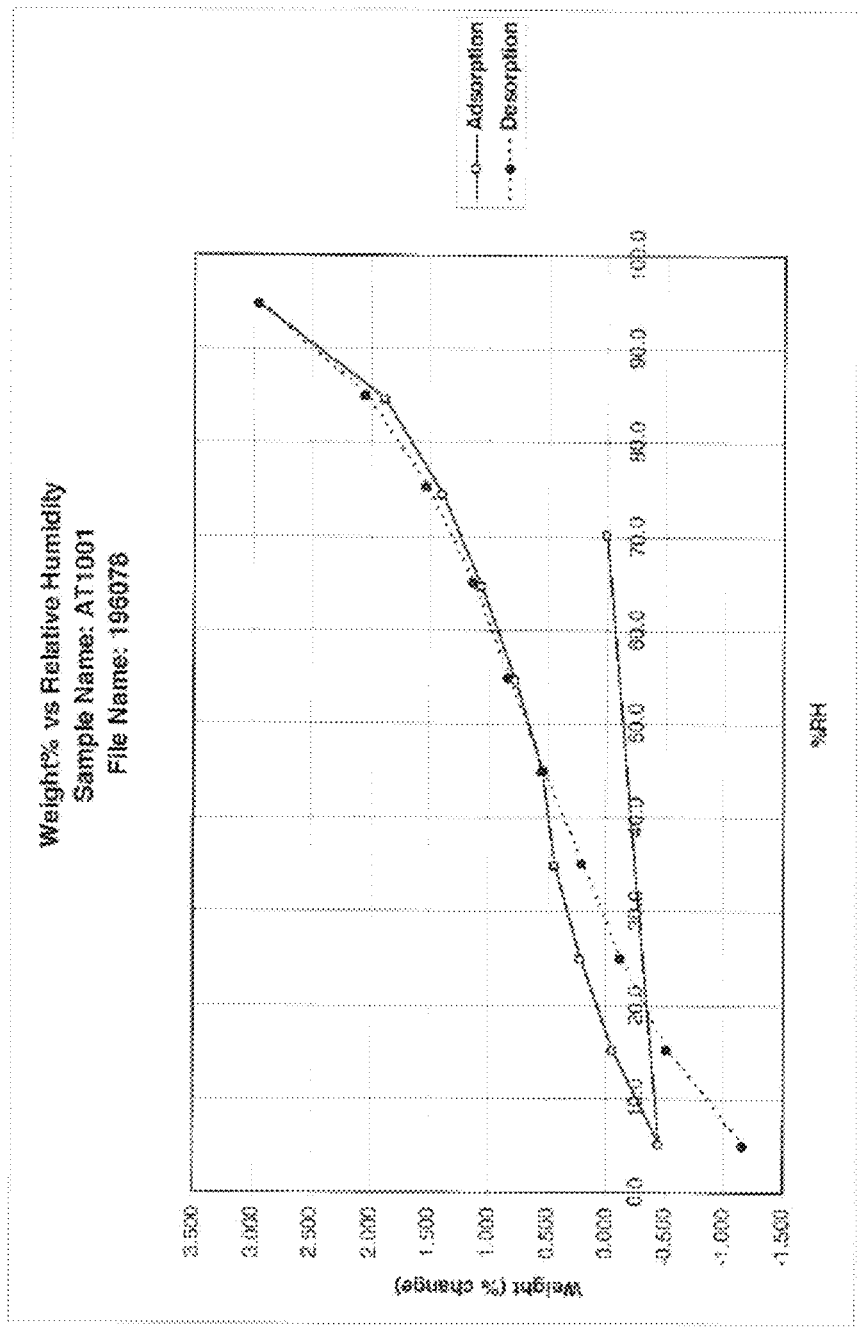
FIG. 13 shows exemplary moisture sorption/desorption data for crystalline Larazotide acetate.

The moisture sorption/desorption data shows a constant weight gain during sorption phase and a constant weight loss during the desorption phase experiment (FIG. 13). XRPD analysis following the moisture sorption experiment indicated the sample was still Form A, suggesting that exposure to humidity does not result in a form change for Form A.

Approximate solubilities of Larazotide acetate Form A in different solvents were determined. Aliquots of the test solvent were added to weighed samples of Larazotide. The samples were sonicated to aid in dissolution. Visual inspection was used to determine if a sample had dissolved. The approximate solubility was calculated from the total amount of solvent added. The solubilities are reported to the nearest mg/mL and are reported as "less than" when dissolution did not occur. Actual solubilities may be greater due to the size of the aliquots added or to slow rate of dissolution.

Larazotide acetate was determined to have low solubility in most solvents tested. The only solvent showing appreciable solubility in this study was trifluoroethanol (4 mg/ml), and that solvent had a slow dissolution rate. Because of the slow rate of dissolution, the solubility in trifluoroethanol is likely higher than reported.

TABLE 7

Solubilities of Form A is Different Solvents

| Solvent | Solubility |
|---|---|
| Acetone | <4 |
| Acetonitrile (ACN) | <4 |
| Dichloromethane (DCM) | <4 |
| Dioxane | <4 |
| Dimethyl sulfoxide (DMSO) | <4 |
| Ethanol (EtOH) | <4 |
| Ethyl acetate (EtOAc) | <4 |
| Methanol (MeOH) | <4 |
| Tetrahydrofuran (THF) | <4 |
| Trifluoroethanol (TFE) | 4 |
| Water | 8 |
| (1:1) DCM/MeOH | <3 |
| (1:1) Water/ACN | <3 |
| (1:1) Water/Dioxane | <3 |
| (1:1) Water/MeOH | <3 |

Figure 14:
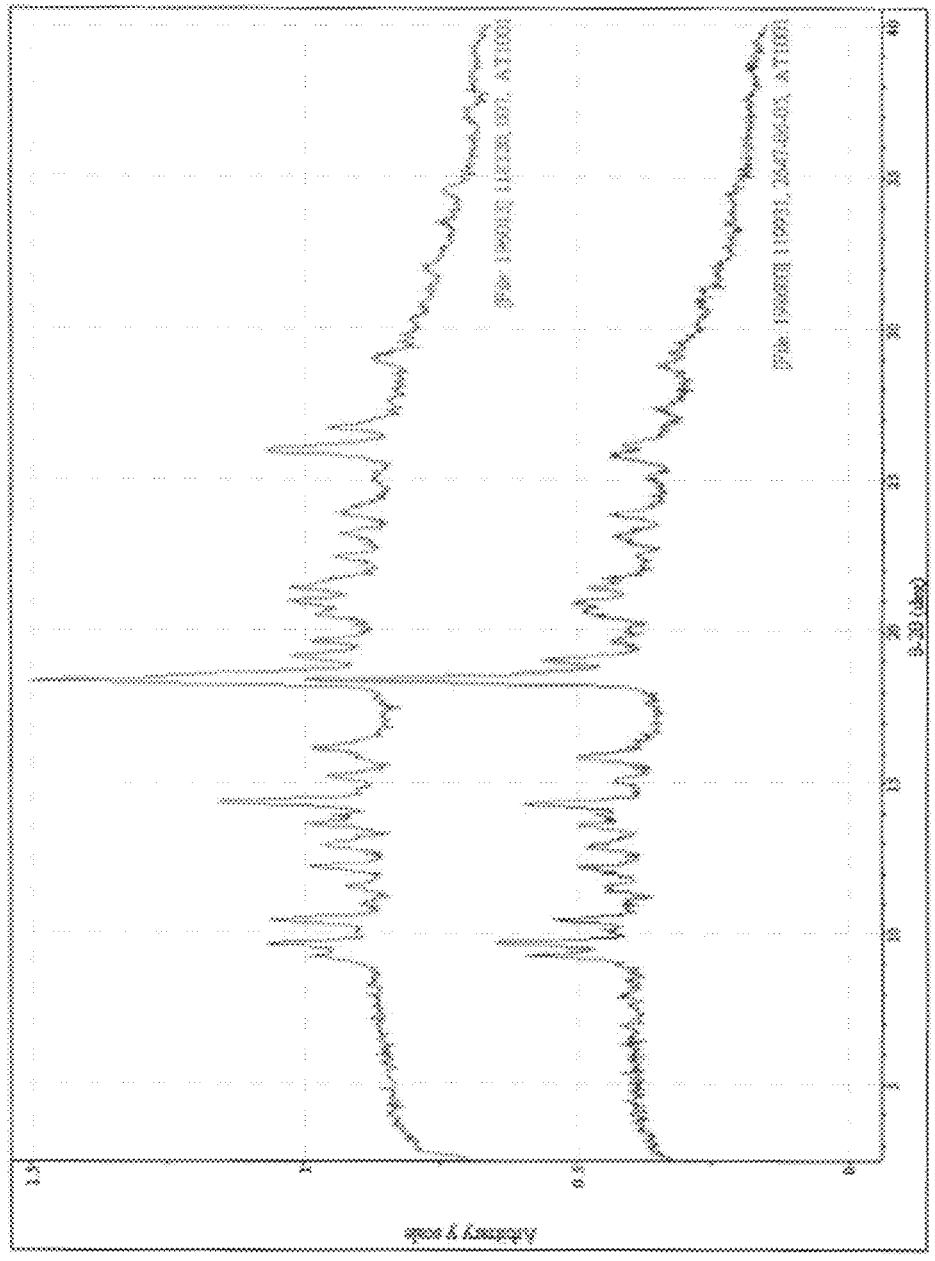
FIG. 14 compares exemplary XRPD patterns of Larazotide acetate Form A (top) and Form A' (bottom).

Three samples of larazotide acetate yielded an XRPD pattern similar, but not identical to that of Form A. This pattern was designated A', and a comparison to the Form A pattern is displayed in FIG. 14. The peaks below ~12.5° 2θ are almost identical between the two patterns, while slight shifts are observed above ~12.5° 2θ. In particular, differences are observed at ~16° 2θ and between 22 and 29° 2θ. These differences may be the result of preferred orientation effects, or they could result from conformational polymorphism given the degrees of freedom of the molecule. Alternatively, the pattern differences may arise from differences in water content.

Nevertheless, it has been found that crystalline larazotide acetate (Form A and Form A') can be described by a XRPD pattern comprising one or more of the following peaks: 9.08±0.2 degrees 2θ, 9.52±0.2 degrees 2θ, 10.34±0.2 degrees 2θ, 14.24±0.2 degrees 2θ, 18.23±0.2 degrees 2θ, 19.08±0.2 degrees 2θ and/or 21.31±0.2 degrees 2θ. In one embodiment, crystalline larazotide acetate can be described by an XRPD pattern comprising a peak at 14.24±0.2 degrees 2θ and one or more of the following peaks at 9.08±0.2 degrees 2θ, 9.52±0.2 degrees 2θ, 10.34±0.2 degrees 2θ, 18.23±0.2 degrees 2θ, 19.08±0.2 degrees 2θ and/or 21.31±0.2 degrees 2θ. In another embodiment, crystalline larazotide acetate can be described by an XRPD pattern comprising peaks at 14.24±0.2 degrees 2θ and 10.34±0.2 degrees 2θ and one or more of the following peaks at: 9.08±0.2 degrees 2θ, 9.52±0.2 degrees 2θ, 18.23±0.2 degrees 2θ, 19.08±0.2 degrees 2θ and/or 21.31±0.2 degrees 2θ. In a further embodiment, crystalline larazotide acetate can be described by an XRPD pattern comprising peaks at 14.24±0.2 degrees 2θ, 10.34±0.2 degrees 2θ, and 9.52±0.2 degrees 2θ and one or more of the following peaks at: 9.08±0.2 degrees 2θ, 18.23±0.2 degrees 2θ, 19.08±0.2 degrees 2θ and/or 21.31±0.2 degrees 2θ. In yet a further embodiment, crystalline larazotide acetate can be described by an XRPD pattern comprising peaks at 14.24±0.2 degrees 2θ, 18.23±0.2 degrees 2θ, 19.08±0.2 degrees 2θ, 10.34±0.2 degrees 2θ and one or more of the following peaks at: 9.08±0.2 degrees 2θ, 9.52±0.2 degrees 2θ, and/or 21.31±0.2 degrees 2θ.

The invention claimed is:

1. A crystalline acetate salt of the peptide Gly-Gly-Val-Leu-Val-Gln-Pro-Gly (SEQ ID NO:1) having an XRPD pattern comprising peaks at 9.08±0.2 degrees 2θ, 9.52±0.2 degrees 2θ, 10.34±0.2 degrees 2θ, and 14.24±0.2 degrees 2θ.

2. A pharmaceutical composition comprising or prepared with the crystalline peptide salt of claim 1.

3. The crystalline acetate salt of claim 1 further comprising one or more of the following peaks: 18.23±0.2 degrees 2θ, 19.08±0.2 degrees 2θ and/or 21.31±0.2 degrees 2θ.

4. The crystalline acetate salt of claim 3 having an XRPD pattern comprising peaks at 14.24±0.2 degrees 2θ and 18.23±0.2 degrees 2θ.

5. The crystalline acetate salt of claim 1, wherein the acetate is present at a concentration of from about 20 to 30 mole %/mole of peptide.

6. The crystalline acetate salt of claim 5, wherein the acetate is present at a concentration of less than about 15 mole %.

7. The crystalline acetate salt of claim 6, wherein the acetate is present at a concentration of less than about 10 mole %.

8. The crystalline acetate salt of claim 7, wherein the acetate is present at a concentration of between about 4 to about 8 mole %.

* * * * *